(12) United States Patent
Grill et al.

(10) Patent No.: US 10,773,084 B2
(45) Date of Patent: *Sep. 15, 2020

(54) NON-REGULAR ELECTRICAL STIMULATION PATTERNS DESIGNED WITH A COST FUNCTION FOR TREATING NEUROLOGICAL DISORDERS

(71) Applicant: Duke University, Durham, NC (US)

(72) Inventors: Warren M. Grill, Chapel Hill, NC (US); David T. Brocker, Cary, NC (US)

(73) Assignee: Duke University, Durham, NC (US)

( * ) Notice: Subject to any disclaimer, the term of this patent is extended or adjusted under 35 U.S.C. 154(b) by 348 days.

This patent is subject to a terminal disclaimer.

(21) Appl. No.: 15/436,948

(22) Filed: Feb. 20, 2017

(65) Prior Publication Data
US 2017/0259067 A1 Sep. 14, 2017

Related U.S. Application Data

(63) Continuation of application No. 15/005,636, filed on Jan. 25, 2016, now Pat. No. 9,572,988, which is a
(Continued)

(51) Int. Cl.
*A61N 1/36* (2006.01)
*A61N 1/05* (2006.01)

(52) U.S. Cl.
CPC ....... *A61N 1/36178* (2013.01); *A61N 1/0534* (2013.01); *A61N 1/36067* (2013.01);
(Continued)

(58) Field of Classification Search
CPC .............. A61N 1/0534; A61N 1/36067; A61N 3608/02; A61N 3608/36125;
(Continued)

(56) References Cited

U.S. PATENT DOCUMENTS 3,833,005 A  9/1974 Wingrove
4,338,945 A  7/1982 Kosugi et al.
(Continued)

FOREIGN PATENT DOCUMENTS

CN  86102850  11/1987
EP   1145735  10/2001
(Continued)

OTHER PUBLICATIONS

Van den Wildenberg, Wery, et al. "Stimulation of the Subthalamic Region Facilitates the Selection and Inhibition of Motor Responses in Parkinson's Disease." Apr. 1, 2006. Journal of Cognitive Neuroscience. vol. 18 Issue 4. 626-636. (Year: 2006).*
(Continued)

*Primary Examiner* — Nicole F Lavert
(74) *Attorney, Agent, or Firm* — McDonald Hopkins LLC

(57) ABSTRACT

Systems and methods for stimulation of neurological tissue generate stimulation trains with temporal patterns of stimulation, in which the interval between electrical pulses (the inter-pulse intervals) changes or varies over time. Compared to conventional continuous, high rate pulse trains having regular (i.e., constant) inter-pulse intervals, the non-regular (i.e., not constant) pulse patterns or trains that embody features of the invention provide a lower average frequency.

19 Claims, 23 Drawing Sheets

Related U.S. Application Data continuation of application No. 14/583,932, filed on Dec. 29, 2014, now Pat. No. 9,242,095, which is a continuation of application No. 13/770,731, filed on Feb. 19, 2013, now Pat. No. 8,923,981, which is a continuation-in-part of application No. 12/587,295, filed on Oct. 5, 2009, now Pat. No. 8,447,405.

(60) Provisional application No. 61/600,264, filed on Feb. 17, 2012, provisional application No. 61/102,575, filed on Oct. 3, 2008.

(52) U.S. Cl.
CPC ..... *A61N 1/36082* (2013.01); *A61N 1/36125* (2013.01); *A61N 1/36128* (2013.01); *A61N 1/36196* (2013.01)

(58) Field of Classification Search
CPC .......... A61N 3608/36128; A61N 3608/36178; A61N 3608/36196
USPC .......................................................... 607/45
See application file for complete search history.

(56) References Cited

U.S. PATENT DOCUMENTS

| | | | |
|---|---|---|---|
| 4,979,507 A | 12/1990 | Heinz | |
| 5,018,524 A | 5/1991 | Gu et al. | |
| 5,073,544 A | 12/1991 | Seto | |
| 5,095,904 A | 3/1992 | Seligman et al. | |
| 5,184,616 A | 7/1993 | Weiss | |
| 5,226,413 A | 7/1993 | Bennett | |
| 5,485,851 A | 1/1996 | Erickson | |
| 5,716,377 A | 2/1998 | Rise et al. | |
| 5,724,985 A | 3/1998 | Snell | |
| 6,066,163 A | 5/2000 | Sasha | |
| 6,560,487 B1 | 5/2003 | McGraw et al. | |
| 6,560,490 B2 | 5/2003 | Grill et al. | |
| 6,738,668 B1 | 5/2004 | Mouchawar | |
| 6,879,860 B2 | 4/2005 | Wakefield | |
| 6,934,580 B1 | 8/2005 | Osorio | |
| 6,944,501 B1 | 9/2005 | Pless | |
| 7,010,351 B2 | 3/2006 | Firlik et al. | |
| 7,191,014 B2 | 3/2007 | Kobayashi et al. | |
| 7,321,796 B2 | 1/2008 | Fink | |
| 7,483,747 B2 | 1/2009 | Gilner et al. | |
| 7,949,397 B1 | 5/2011 | Wenzel | |
| 7,970,477 B2 | 6/2011 | Loeb | |
| 8,073,544 B2 | 12/2011 | Pless | |
| 8,355,789 B2 | 1/2013 | Werder et al. | |
| 8,447,405 B2 | 5/2013 | Grill et al. | |
| 8,694,106 B2 | 4/2014 | Pless | |
| 8,798,755 B2 | 8/2014 | Grill et al. | |
| 8,923,981 B2 | 12/2014 | Grill, Jr. et al. | |
| 9,089,708 B2 | 7/2015 | Grill | |
| 9,242,095 B2 | 1/2016 | Grill et al. | |
| 9,259,579 B2 | 2/2016 | Grill et al. | |
| 9,572,988 B2 | 2/2017 | Grill | |
| 9,744,363 B2 | 8/2017 | Grill | |
| 10,086,204 B2 | 10/2018 | Grill | |
| 10,086,205 B2 | 10/2018 | Grill | |
| 2002/0077670 A1 | 6/2002 | Archer | |
| 2002/0177882 A1 | 11/2002 | DiLorenzo | |
| 2003/0135248 A1 | 7/2003 | Stypulkowski | |
| 2004/0158298 A1 | 8/2004 | Gliner et al. | |
| 2004/0243192 A1 | 12/2004 | Hepp | |
| 2004/0249422 A1 | 12/2004 | Gliner et al. | |
| 2005/0060009 A1 | 3/2005 | Goetz | |
| 2005/0222641 A1 | 10/2005 | Pless | |
| 2005/0228453 A1 | 10/2005 | Havel | |
| 2005/0228461 A1 | 10/2005 | Osorio | |
| 2006/0015153 A1* | 1/2006 | Gliner | A61N 1/3606 607/45 |
| 2006/0017749 A1 | 1/2006 | McIntyre | |
| 2006/0111759 A1 | 5/2006 | Hoyme | |
| 2006/0212089 A1 | 9/2006 | Tass | |
| 2007/0067004 A1 | 3/2007 | Boveja | |
| 2007/0198066 A1 | 8/2007 | Greenberg | |
| 2007/0288064 A1 | 12/2007 | Butson et al. | |
| 2008/0045775 A1 | 2/2008 | Lozano | |
| 2009/0036949 A1 | 2/2009 | Kokones | |
| 2009/0082640 A1 | 3/2009 | Kovach | |
| 2009/0110958 A1 | 4/2009 | Hyde | |
| 2009/0131993 A1 | 5/2009 | Rousso et al. | |
| 2009/0264954 A1 | 10/2009 | Rise | |
| 2010/0042194 A1 | 2/2010 | Ayal | |
| 2010/0121407 A1 | 5/2010 | Pfaff | |
| 2010/0121416 A1 | 5/2010 | Lee | |
| 2010/0152807 A1 | 6/2010 | Grill et al. | |
| 2010/0312303 A1 | 12/2010 | York | |
| 2010/0331916 A1 | 12/2010 | Parramon | |
| 2011/0093041 A1 | 4/2011 | Straka et al. | |
| 2011/0106213 A1 | 5/2011 | Davis | |
| 2011/0184486 A1 | 7/2011 | De Ridder | |
| 2011/0196441 A1 | 8/2011 | Ryu | |
| 2011/0270348 A1 | 11/2011 | Goetz | |
| 2012/0004707 A1 | 1/2012 | Lee | |
| 2012/0016435 A1 | 1/2012 | Rom | |
| 2012/0290041 A1 | 11/2012 | Kim | |
| 2013/0006330 A1 | 1/2013 | Wilder | |
| 2013/0102919 A1 | 4/2013 | Schiff | |
| 2013/0231715 A1 | 9/2013 | Grill | |
| 2013/0345773 A1 | 12/2013 | Grill et al. | |
| 2014/0257428 A1 | 9/2014 | Zhu | |
| 2014/0353944 A1 | 12/2014 | Grill et al. | |
| 2017/0361099 A1 | 12/2017 | De Ridder | |
| 2018/0064944 A1 | 3/2018 | Grill | |

FOREIGN PATENT DOCUMENTS

| | | |
|---|---|---|
| EP | 2766087 | 8/2014 |
| JP | 2008506464 | 3/2008 |
| WO | 2006019764 | 2/2006 |
| WO | 2010039274 | 4/2010 |
| WO | 2014130071 | 8/2014 |

OTHER PUBLICATIONS

Feng, Xiao-jiang, et al. "Toward closed-loop optimization of deep brain stimulation for Parkinson's disease: concepts and lessons from a computational model." Feb. 23, 2007. Journal of Neural Engineering. vol. 4. L14-L21. (Year: 2007).*

International Search Report and the Written Opinion of the International Searching Authority, PCT/US2013/046183, Duke University, dated Oct. 4, 2013.

International Search Report and the Written Opinion of the International Searching Authority, PCT/US2012/059787, Duke University, dated Jan. 4, 2013.

International Preliminary Examination Report, PCT/US2009/05459, Duke University, dated Jan. 11, 2011.

International Search Report and the Written Opinion of the International Searching Authority, PCT/US2009/05459, Duke University, dated Dec. 3, 2009.

Extended European Search Report, Application No. 09818122.5-1652/2340078, Duke University, dated Aug. 2, 2013.

Rubin, Jonathan et al., High Frequency Stimulation of the Subthalamic Nucleus Eliminates Pathological Thalamic Rhythmicity in a Computational Model, Journal of Computational Neuroscience, vol. 16, pp. 211-235, 2004.

McIntyre, Cameron et al., Cellular Effects of Deep Brain Stimulation: Model-Based Analysis of Activation and Inhibition, J. Neurophysiol, vol. 91, pp. 1457-1469, 2004.

Birdno, Merrill Jay, Analyzing the Mechanisms of Action of Thalamic Deep Brain Stimulation: Computational and Clinical Studies, Ph. D. Dissertation, Department of Biomedical Engineering, Duke University, Durham, NC, USA, Aug. 2009.

Constantoyannis, Constantine, et al., Tremor Induced by Thalamic Deep Brain Stimulation in Patients with Complex Regional Facial Pain, Movement Disorders, vol. 19, No. 8, pp. 933-936, 2004.

(56) References Cited

OTHER PUBLICATIONS

Benabid, Alim et al., Long-term suppression of tremor by chronic stimulation of the ventral intermediate thalamic nucleus, The Lancet, vol. 337, pp. 403-406, Feb. 16, 1991.
Davis, Lawrence, Handbook of Genetic Algorithms, Van Nostrand Reinhold, NY, pp. 1-402, 1991.
Dorval, Alan et al., Deep Brain Stimulation Alleviates Parkinsonian Bradykinesia by Regularizing Pallidal Activity, J. Neurophysiol, vol. 104, pp. 911-921, 2010.
Fogelson, Noa et al., Frequency dependent effects of subthalamic nucleus stimulation in Parkinson's disease, Neuroscience Letters 382, 5-9, 2005.
Grefenstette, John, Optimization of Control Parameters for Genetic Algorithms, IEEE Transactions on Systems, Man, and Cybernetics, vol. SMC-16, No. 1, pp. 122-128, Jan./Feb. 1986.
Feng, Xiao-jiang et al., Optimal Deep Brain Stimulation of the Subthalamic Nucleus—a Computational Study, Journal of Computational Neuroscience, 23(3):265-282, Jan. 9, 2007.
Grill, W.M. et al., Effect of waveform on tremor suppression and paresthesias evoked by thalamic deep brain stimulation (dbs), Society for Neuroscience Abstract 29, 2003.
Kuncel, Alexis et al., Clinical Response to Varying the Stimulus Parameters in Deep Brain Stimulation for Essential Tremor, Movement Disorders, vol. 21, No. 11, pp. 1920-1928, 2006.
Kupsch, A. et al., The effects of frequency in pallidal deep brain stimulation for primary dystonia, J. Neurol 250:1201-1205, 2003.
Tinnerman, Lars et al., The cerebral oscillatory network of parkinsonian resting tremor, Brain, 126, pp. 199-212, 2003.
Limousin, Patricia et al., Effect on parkinsonian signs and symptoms of bilateral subthalamic nucleus stimulation, The Lancet, vol. 345, pp. 91-95, Jan. 14, 1995.
SA/US,International Search Report and Written Opinion prepared for PCT/US2014/072112, dated Apr. 16, 2015.
International Preliminary Report on Patentability for PCT/US11/38416, dated May 3, 2012.
International Search Report/Written Opinion dated Dec. 7, 2011 in International Patent Application No. PCT/US11/38416.
Extended European Search Report for Application 13875748.9 PCT/US2013046183, dated Mar. 9, 2016, European Patent Office, Germany.
International Searching Authority, US Patent Office; International Search Report and Written Opinion for PCT/US2014/038809, dated Dec. 15, 2014, 19 pages.
Feng et al. "Toward closed-loop optimization of deep brain stimulation for Parkinson's disease: concepts and lessons from a computational model." J. Neural Eng. 4 (2007) L14-L21. Feb. 23, 2007.
So et al. "Relative contributions of local cell and passing fiber activation and silencing to changes in thalamic fidelity luring deep brain stimulation and lesioning: a computational modeling study". Comput Neurosci (2012) 32:499-519. Oct. 5, 2011.
Kent et al. "Instrumentation to Record Evoked Potentials for Closed-Loop Control of Deep Brain Stimulation". Conf Proc IEEE Eng Med Biol Soc, 2011; 2011: 6777-6780. doi:10.1109/IEMBS.2011.6091671.
Dorval et al. "Deep Brain Stimulation that Abolishes Parkinsonian Activity in Basal Ganglia Improves Thalamic Relay Fidelity in a Computational Circuit". Conf Proc IEEE Eng Med Biol Soc. 2009; 1: 4230. doi:10.11091EMB5.2009.5333611.
Brocker, David. et al., Improved Efficacy of Temporally Non-Regular Deep Brain Stimulation in Parkinson's Disease, Department of Biomedical Engineering, Duke University, Durham NC 27708-0281, pp. 1-34, 2012.
European Patent Office, Supplementary European Search Report, EP14874436, dated Jan. 17, 2018.
European Patent Office, European Search Report, EP 17001653, dated Jan. 4, 2018.

\* cited by examiner

NON-REGULAR ELECTRICAL STIMULATION PATTERNS DESIGNED WITH A COST FUNCTION FOR TREATING NEUROLOGICAL DISORDERS

CROSS-REFERENCE TO RELATED APPLICATION

This application is a continuation of U.S. patent application Ser. No. 15/005,636, filed on Jan. 25, 2015, granted as U.S. Pat. No. 9,572,988, and entitled "A Neural Stimulation Device with Non-Regular Stimulation Patterns Designed with a Cost Function for Treating Neurological Disorders," which is a continuation of U.S. patent application Ser. No. 14/583,932, filed on Dec. 29, 2014, granted as U.S. Pat. No. 9,242,095, and entitled "A Neural Stimulation Device with Non-Regular Stimulation Patterns Designed with a Cost Function for Treating Neurological Disorders," which is a continuation of U.S. patent application Ser. No. 13/770,731, filed on Feb. 19, 2013, granted as U.S. Pat. No. 8,923,981, and entitled "Non-Regular Electrical Stimulation Patterns Designed With a Cost Function for Treating Neurological Disorders," which claims the benefit of U.S. Provisional Application Ser. No. 61/600,264, entitled "Non-Regular Electrical Stimulation Patterns for Treating Neurological Disorders" filed on Feb. 17, 2012 and which is a continuation-in-part of co-pending U.S. patent application Ser. No. 12/587,295, granted as U.S. Pat. No. 8,447,405, filed Oct. 5, 2009, and entitled "Non-Regular Electrical Stimulation Patterns for Treating Neurological Disorders," which claimed the benefit of U.S. Provisional Patent Application Ser. No. 61/102,575, filed Oct. 3, 2008, and entitled "Stimulation Patterns For Treating Neurological Disorders Via Deep Brain Stimulation," which are all incorporated herein by reference.

FIELD OF INVENTION

This invention relates to systems and methods for stimulating nerves in animals, including humans.

BACKGROUND

Deep Brain Stimulation (DBS) has been found to be successful in treating a variety of brain-controlled disorders, including movement disorders. Generally, such treatment involves placement of a DBS type lead into a targeted region of the brain through a burr hole drilled in the patient's skull, and the application of appropriate stimulation through the lead to the targeted region.

Presently, in DBS, beneficial (symptom-relieving) effects are observed primarily at high stimulation frequencies above 100 Hz that are delivered in stimulation patterns or trains in which the interval between electrical pulses (the inter-pulse intervals) is constant over time. The trace of a conventional stimulation train for DBS is shown in FIG. 2. The beneficial effects of DBS on motor symptoms are only observed at high frequencies, while low frequency stimulation has generally been thought to exacerbate symptoms. For instance, thalamic DBS at less than or equal to 50 Hz has been shown to increase tremor in patients with essential tremor. Similarly, 50 Hz DBS has been shown to produce or induce tremor in pain patients receiving simulation of the ventral posterior medial nucleus of the thalamus (VPM), but the tremor disappears when the frequency is increased. Likewise, DBS of the subthalamic nucleus (STN) at 10 Hz has been shown to worsen akinesia in patients with Parkinson's disease (PD), while DBS at 130 Hz leads to significant improvement in motor function. Similarly, relatively high frequency stimulation of the globus pallidus (GP) at or above 130 Hz has been shown to improve dystonia, whereas stimulation at either 5 or 50 Hz may lead to significant worsening.

Model studies also indicate that the masking of pathological burst activity occurs only with sufficiently high stimulation frequencies. See Grill et al. 2004, FIG. 1. Responsiveness of tremor to changes in DBS amplitude and frequency are strongly correlated with the ability of applied stimuli to mask neuronal bursting. See Kuncel et al. 2007, FIG. 2.

Although effective, conventional high frequency stimulation generates stronger side-effects than low frequency stimulation, and the therapeutic window between the voltage that generates the desired clinical effect(s) and the voltage that generates undesired side effects decreases with increasing frequency. Precise lead placement therefore becomes important. Further, high stimulation frequencies increase power consumption. The need for higher frequencies and increased power consumption shortens the useful lifetime and/or increases the physical size of battery-powered implantable pulse generators. The need for higher frequencies and increased power consumption requires a larger battery size, and/or frequent charging of the battery, if the battery is rechargeable, or replacement of the battery if it is not rechargeable.

SUMMARY

The invention provides stimulation patterns or trains with different temporal patterns of stimulation than conventional stimulation trains. The invention also provides methodologies to identify and characterize stimulation patterns or trains that produce desired relief of symptoms, while reducing the average stimulation frequency.

According to one aspect of the invention, the intervals between stimulation pulses in a pulse pattern or train (in shorthand called "the inter-pulse intervals") is not constant over time, but changes or varies over time. These patterns or trains are consequently called in shorthand "non-regular." According to this aspect of the invention, the non-regular (i.e., not constant) pulse patterns or trains provide a lower average frequency for a given pulse pattern or train, compared to conventional continuous, high rate pulse trains having regular (i.e., constant) inter-pulse intervals. Having a lower average frequency, the non-regular stimulus patterns or trains make possible an increase in the efficacy of stimulation by reducing the intensity of side effects; by increasing the dynamic range between the onset of the desired clinical effect(s) and side effects (and thereby reducing sensitivity to the position of the lead electrode); and by decreasing power consumption, thereby providing a longer useful battery life and/or a smaller implantable pulse generator, allowing battery size reduction and/or, for rechargeable batteries, longer intervals between recharging.

The non-regular stimulation patterns or trains can be readily applied to deep brain stimulation, to treat a variety of neurological disorders, such as Parkinson's disease, movement disorders, epilepsy, and psychiatric disorders such as obsessive-compulsion disorder and depression. The non-regular stimulation patterns or trains can also be readily applied to other classes electrical stimulation of the nervous system including, but not limited to, cortical stimulation, spinal cord stimulation, and peripheral nerve stimulation (including sensory and motor), to provide the attendant benefits described above and to treat diseases such as but not limited to Parkinson's Disease, Essential Tremor, Movement Disorders, Dystonia, Epilepsy, Pain, psychiatric disorders such as Obsessive Compulsive Disorder, Depression, and Tourette's Syndrome.

According to another aspect of the invention, systems and methodologies make it possible to determine the effects of the temporal pattern of DBS on simulated and measured neuronal activity, as well as motor symptoms in both animals and humans. The methodologies make possible the qualitative determination of the temporal features of stimulation trains.

The systems and methodologies described herein employ a genetic algorithm, coupled to a computational model of DBS of the STN, to develop non-regular patterns of stimulation that produced efficacy (as measured by a low error function, E) at lower stimulation frequencies, F. The error function, E, is a quantitative measure from the model which assesses how faithfully the thalamus transmitted motor commands that are generated by inputs from the cortex. A very high correlation exists between E and symptoms in persons with PD, and therefore E is a valid predictor for the efficacy of a stimulation train in relieving symptoms (see Dorval et al., 2007).

Previous efforts (see Feng et al. 2007) sought to design stimulation trains that minimized the total current injection. The systems and methodologies disclosed herein include an objective function that maximizes therapeutic benefit (by minimizing the error function) and improves stimulation efficiency (by reducing the stimulation frequency), using a model of the STN that reproduces the frequency tuning of symptom reduction that has been documented clinically. In contrast, the Feng et al. model showed, incorrectly, symptom reduction with regular, low frequency stimulation. The inventors have identified novel non-regular temporal patterns of stimulation, while Feng et al. identified regular low frequency (~10 Hz) trains that previous clinical work has demonstrated to be ineffective.

A neural stimulation device may include a pulse generator configured to transmit a first temporal pattern of stimulation for application to neurological tissue having a first non-regular pulse train, the first non-regular pulse train including a first plurality of single pulses (first singlets) and embedded first multiple pulse groups (first n-lets), with non-regular inter-pulse intervals between the first singlets and first n-lets, as well as non-regular inter-pulse intervals within the first n-lets themselves. The pulse generator may also be configured to transmit a second temporal pattern of stimulation for application to neurological tissue having a second non-regular pulse train, the second non-regular pulse train including a second plurality of single pulses (second singlets) and embedded second multiple pulse groups (second n-lets), with non-regular inter-pulse intervals between second singlets and second n-lets, as well as non-regular inter-pulse intervals within the second n-lets themselves, the second temporal pattern adapted from applying a model-based optimization technique after application of the first temporal pattern of stimulation.

A method for stimulation of a targeted neurological tissue region may include the steps of applying electrical current to a targeted neurological tissue region of an animal using a pulse generator according to a first non-regular pulse train including a first plurality of single pulses (first singlets) and embedded first multiple pulse groups (first n-lets), with non-regular inter-pulse intervals between the first singlets and first n-lets, as well as non-regular inter-pulse intervals within the first n-lets themselves, and analyzing results of the first non-regular pulse train. The method may further include the steps of applying a model-based optimization technique determining a second non-regular pulse trains including a second plurality of single pulses (second singlets) and embedded second multiple pulse groups (second n-lets), with non-regular inter-pulse intervals between second singlets and second n-lets, as well as non-regular inter-pulse intervals within the second n-lets themselves, and applying electrical current to the targeted neurological tissue region of the animal using the pulse generator according to the second non-regular pulse train.

A neural stimulation device may include a pulse generator configured to apply a first non-regular pulse train, having at least one first singlet spaced apart by a first inter-pulse singlet interval and at least one first n-let having, for each n-let, two or more pulses spaced apart by a first inter-pulse interval that is less than the first singlet inter-pulse interval. The pulse generator may also be configurable to apply a second non-regular pulse train, having at least one second singlet spaced apart by a second inter-pulse singlet interval and at least one second n-let having, for each n-let, two or more pulses spaced apart by a second inter-pulse interval that is less than the second singlet inter-pulse interval, the second non-regular pulse trail based upon an analysis of the first non-regular pulse train. The neural stimulation device may also include at least one input configured to operatively connect with at least one electrode.

BRIEF DESCRIPTION OF THE DRAWINGS

Operation of the invention may be better understood by reference to the detailed description taken in connection with the following illustrations, wherein.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Figure 1:
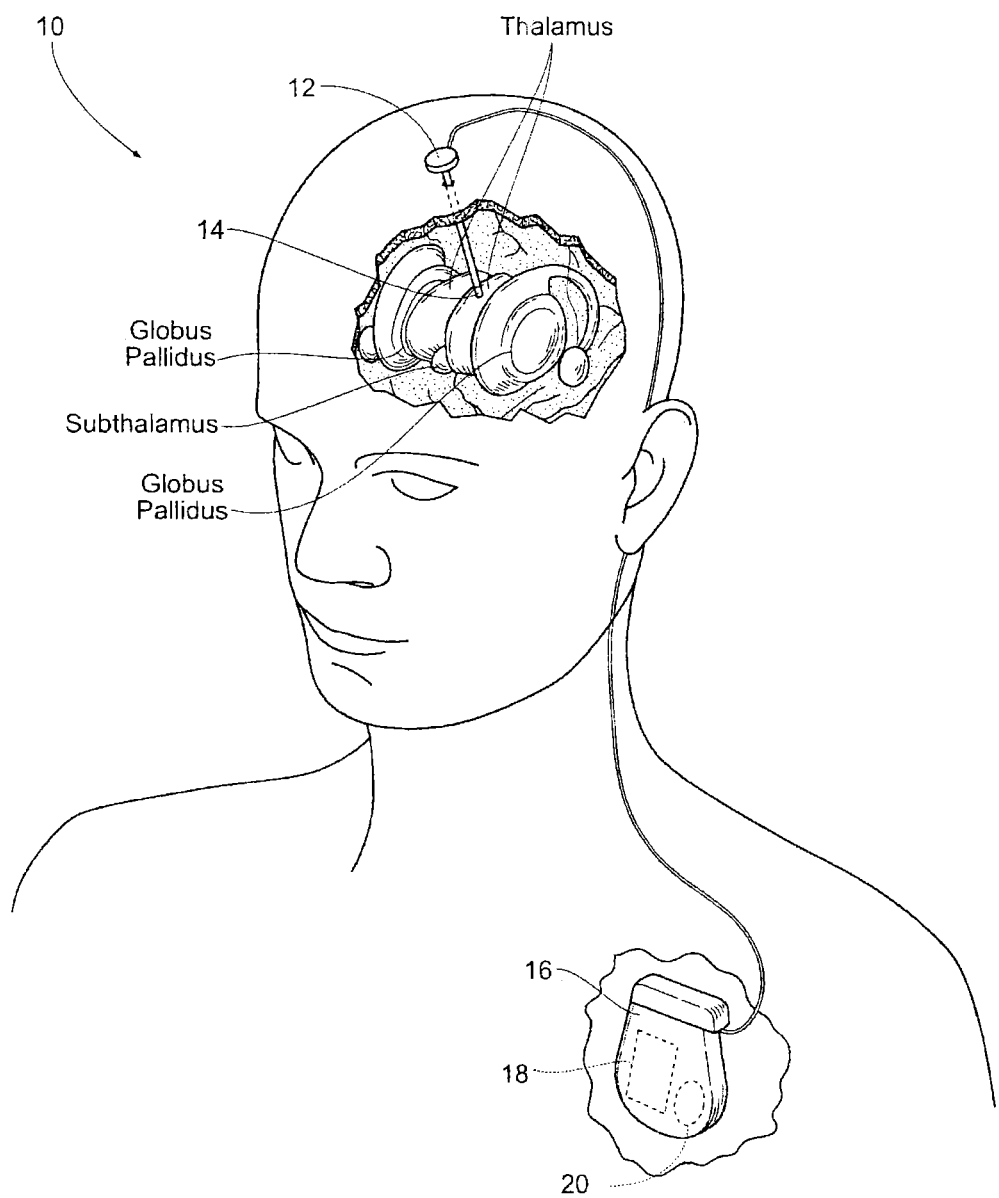
FIG. 1 is an anatomic view of a system for stimulating tissue of the central nervous system that includes an lead implanted in brain tissue coupled to a pulse generator that is programmed to provide non-regular (i.e., not constant) pulse patterns or trains, in which the interval between electrical pulses (the inter-pulse intervals) changes or varies over time.

FIG. 1 is a system 10 for stimulating tissue of the central nervous system. The system may include a lead 12 placed in a desired position in contact with central nervous system tissue. In the illustrated embodiment, the lead 12 may be implanted in a region of the brain, such as the thalamus, subthalamus, or globus pallidus for the purpose of deep brain stimulation. However, it should be understood, the lead 12 may be implanted in, on, or near the spinal cord; or in, on, or near a peripheral nerve (sensory or motor) for the purpose of selective stimulation to achieve a therapeutic purpose.

The distal end of the lead 12 may carry one or more electrodes 14 to apply electrical pulses to the targeted tissue region. The electrical pulses may be supplied by a pulse generator 16 coupled to the lead 12.

In the illustrated embodiment, the pulse generator 16 may be implanted in a suitable location remote from the lead 12, e.g., in the shoulder region. It should be appreciated, however, that the pulse generator 16 may be placed in other regions of the body, i.e., implanted in any suitable location, or externally.

When implanted, the case of the pulse generator 16 may serve as a reference or return electrode. Alternatively, the lead 12 may include a reference or return electrode (comprising a bi-polar arrangement), or a separate reference or return electrode may be implanted or attached elsewhere on the body (comprising a mono-polar arrangement).

The pulse generator 16 may include an on-board, programmable microprocessor 18, which carries embedded code. The code may express pre-programmed rules or algorithms under which a desired electrical stimulation waveform pattern or train is generated and distributed to the electrode(s) 14 on the lead 12. According to these programmed rules, the pulse generator 16 may direct the prescribed stimulation waveform patterns or trains through the lead 12 to the electrode(s) 14, which serve to selectively stimulate the targeted tissue region. The code may be preprogrammed by a clinician to achieve the particular physiologic response desired.

In the illustrated embodiment, an on-board battery 20 may supply power to the microprocessor 18. Currently, batteries 20 must be replaced every 1 to 9 years, depending on the stimulation parameters needed to treat a disorder. When the battery life ends, the replacement of batteries requires another invasive surgical procedure to gain access to the implanted pulse generator. As will be described, the system 10 makes possible, among its several benefits, an increase in battery life.

Figure 2:
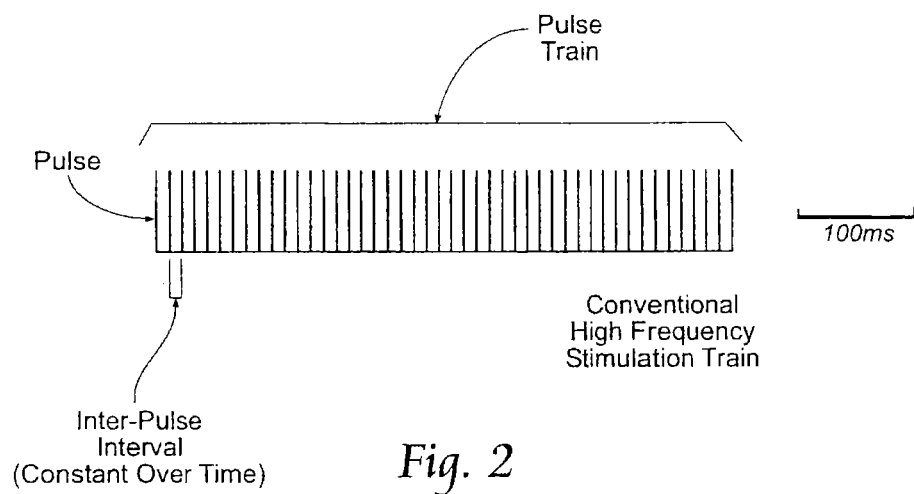
FIG. 2 is a diagrammatic trace that shows a conventional regular high frequency stimulation train, in which the interval between electrical pulses (the inter-pulse intervals) is constant.
Figure 3:
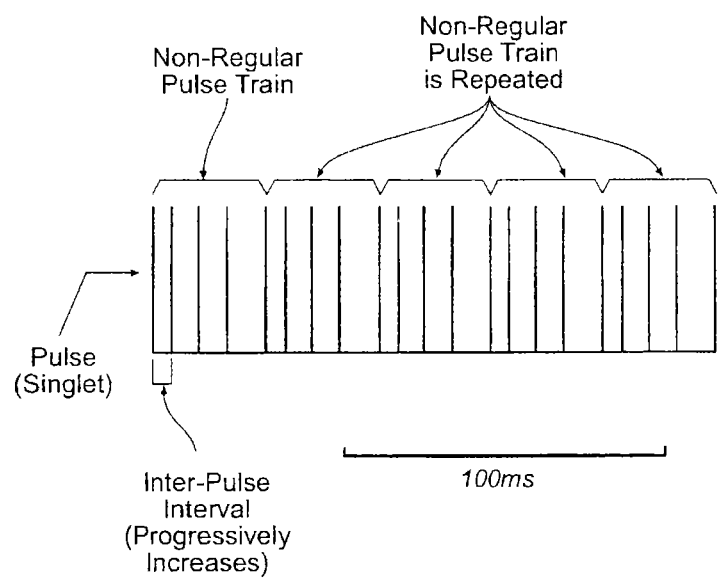
FIG. 3 is a diagrammatic trace showing a representative example of a repeating non-regular pulse pattern or train in which the inter-pulse intervals are linearly cyclically ramped over time.
Figure 4:
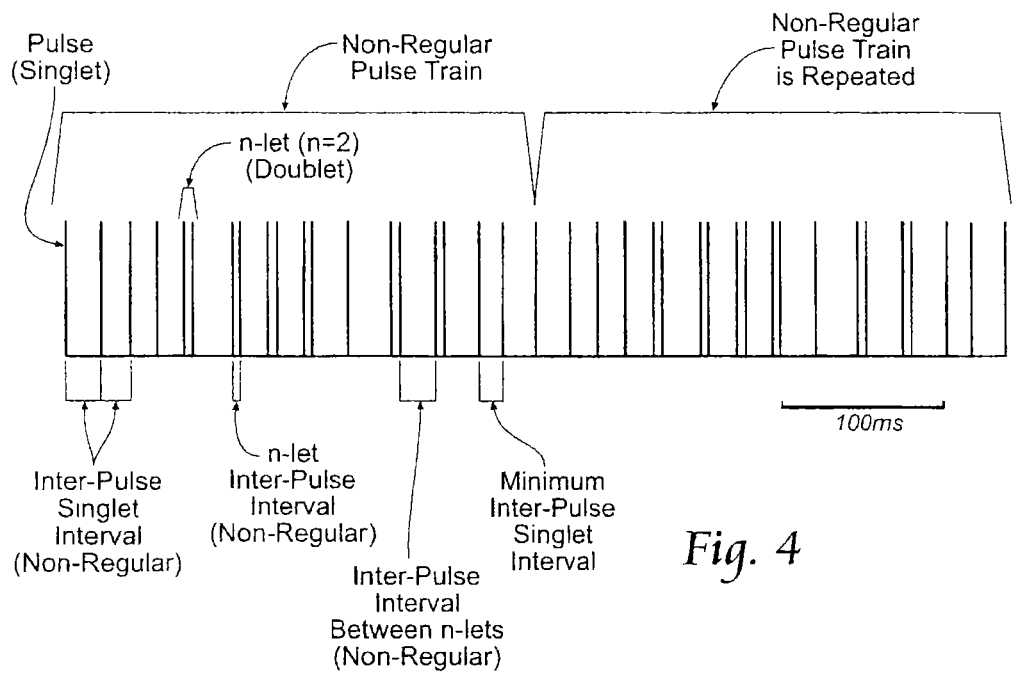
FIGS. 4 and 5 are diagrammatic traces showing other representative examples of repeating non-regular pulse patterns or trains comprising within, a single pulse train, a combination of single pulses (singlets) and embedded multiple pulse groups (n-lets), with non-regular inter-pulse intervals between singlets and n-lets as well as non-regular inter-pulse intervals within the multiple pulse n-lets.
Figure 5:
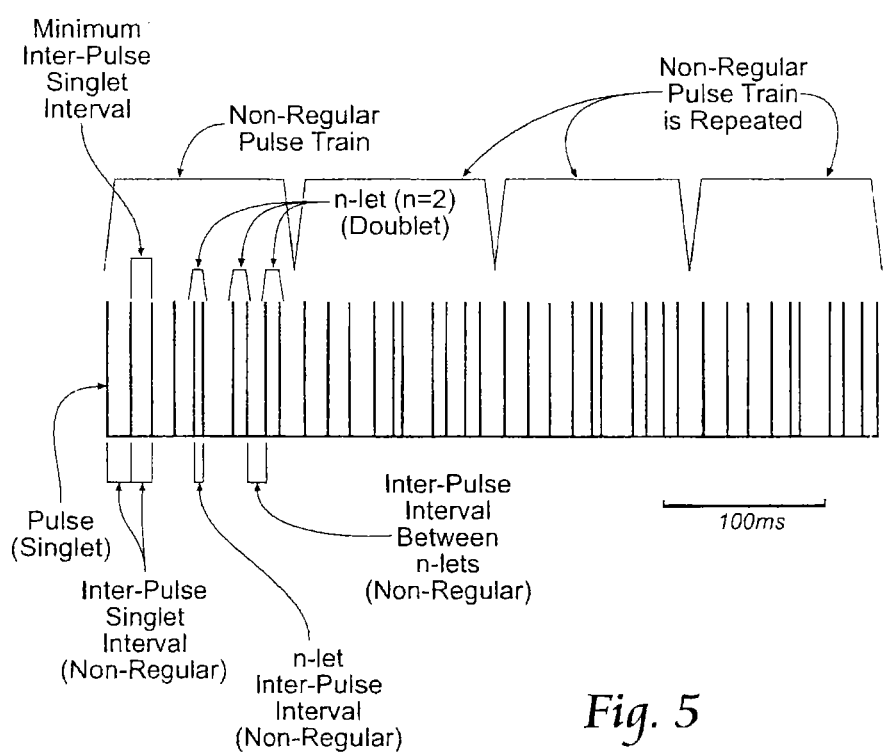

The stimulation waveform pattern or train generated by the pulse generator differs from convention pulse patterns or trains in that the waveform comprises repeating non-regular (i.e., not constant) pulse patterns or trains, in which the interval between electrical pulses (the inter-pulse intervals or IPI) changes or varies over time. Examples of these repeating non-regular pulse patterns or trains are shown in FIGS. 3 to 5. Compared to conventional pulse trains having regular (i.e., constant) inter-pulse intervals (as shown in FIG. 2), the non-regular (i.e., not constant) pulse patterns or trains provide a lower average frequency for a given pulse pattern or train, where the average frequency for a given pulse train (expressed in hertz or Hz) is defined as the sum of the inter-pulse intervals for the pulse train in seconds ($\Sigma_{IPI}$) divided by the number of pulses (n) in the given pulse train, or ($\Sigma_{IPI}$)/n. A lower average frequency makes possible a reduction in the intensity of side effects, as well as an increase in the dynamic range between the onset of the desired clinical effect(s) and side effects, thereby increasing the clinical efficacy and reducing sensitivity to the position of the electrode(s). A lower average frequency brought about by a non-regular pulse pattern or train also leads to a decrease in power consumption, thereby prolonging battery life and reducing battery size.

The repeating non-regular (i.e., not constant) pulse patterns or trains can take a variety of different forms. For example, as will be described in greater detail later, the inter-pulse intervals can be linearly cyclically ramped over time in non-regular temporal patterns (growing larger and/or smaller or a combination of each over time); or be periodically embedded in non-regular temporal patterns comprising clusters or groups of multiple pulses (called n-lets), wherein n is two or more. For example, when n=2, the n-let can be called a doublet; when n=3, the n-let can be called a triplet; when n=4, the n-let can be called a quadlet; and so on. The repeating non-regular pulse patterns or trains can comprise combinations of single pulses (called singlets) spaced apart by varying non-regular inter-pulse intervals and n-lets interspersed among the singlets, the n-lets themselves being spaced apart by varying non-regular inter-pulse intervals both between adjacent n-lets and between the n pulses embedded in the n-let. If desired, the non-regularity of the pulse pattern or train can be accompanied by concomitant changes in waveform and/or amplitude, and/or duration in each pulse pattern or train or in successive pulse patterns or trains.

Each pulse comprising a singlet or imbedded in an n-let in a given train comprises a waveform that can be monophasic, biphasic, or multiphasic. Each waveform possesses a given amplitude (expressed, e.g., in amperes) that can, by way of example, range from 10 μa ($E^{-6}$) to 10 ma ($E^{-3}$). The amplitude of a given phase in a waveform can be the same or differ among the phases. Each waveform also possesses a duration (expressed, e.g., in seconds) that can, by way of example, range from 10 μs ($E^{-6}$) to 2 ms ($E^{-3}$). The duration of the phases in a given waveform can likewise be the same or different. It is emphasized that all numerical values expressed herein are given by way of example only. They can be varied, increased or decreased, according to the clinical objectives.

When applied in deep brain stimulation, it is believed that repeating stimulation patterns or trains applied with non-regular inter-pulse intervals can regularize the output of disordered neuronal firing, to thereby prevent the generation and propagation of bursting activity with a lower average stimulation frequency than required with conventional constant frequency trains, i.e., with a lower average frequency than about 100 Hz. FIG. 3 shows a representative example of a repeating non-regular pulse pattern or train in which the inter-pulse intervals are linearly cyclically ramped over time. As shown in FIG. 3, the pulse pattern or train includes singlet pulses (singlets) spaced apart by progressively increasing inter-pulse intervals providing a decrease in frequency over time, e.g., having an initial instantaneous frequency of 140 Hz, decreasing with doubling inter-pulse intervals, to a final instantaneous frequency of 40 Hz. The inter-pulse intervals can vary within a specified range selected based upon clinical objections, e.g., not to exceed 25 ms, or not to exceed 100 ms, or not to exceed 200 ms, to take into account burst responses and subsequent disruption of thalamic fidelity. The non-regular pulse trains repeat themselves for a clinically appropriate period of time. As shown in FIG. 3, the first pulse train comprises progressively increasing inter-pulse intervals from smallest to largest, followed immediately by another essentially identical second pulse train comprising progressively increasing inter-pulse intervals from smallest to largest, followed immediately by an essentially identical third pulse train, and so on. Therefore, between successive pulse trains, there is an instantaneous change from the largest inter-pulse interval (at the end of one train) to the smallest inter-pulse interval (at the beginning of the next successive train). The train shown in FIG. 3 has an average frequency of 85 Hz and is highly non-regular, with a coefficient of variation (CV) of about 0.5. As is demonstrated in the following Example (Batch 3), the increased efficiency of the pulse train shown in FIG. 3 (due to the lower average frequency) also can provide greater efficacy, as compared to a constant 100 Hz pulse pattern.

The train shown in FIG. 3 exploits the dynamics of burst generation in thalamic neurons. The early high frequency phase of the train masks intrinsic activity in subthalamic nucleus (STN) neurons, and the inter-pulse interval increases reduce the average frequency. A family of trains can be provided by varying the initial frequency, final frequency, and rate of change within the train, with the objective to prevent thalamic bursting with a lower average stimulation frequency than required with constant frequency trains.

FIGS. 4 and 5 show other representative examples of repeating non-regular pulse patterns or trains. The pulse trains in FIGS. 4 and 5 comprise within, a single pulse train, a combination of single pulses (singlets) and embedded multiple pulse groups (n-lets), with non-regular inter-pulse intervals between singlets and n-lets, as well as non-regular inter-pulse intervals within the n-lets themselves. The non-regular pulse trains repeat themselves for a clinically appropriate period of time.

The non-regular pulse train can be characterized as comprising one or more singlets spaced apart by a minimum inter-pulse singlet interval and one or more n-lets comprising, for each n-let, two or more pulses spaced apart by an inter-pulse interval (called the "n-let inter-pulse interval") that is less than the minimum singlet inter-pulse interval.

The n-let inter-pulse interval can itself vary within the train, as can the interval between successive n-lets or a successive n-lets and singlets. The non-regular pulse trains comprising singlets and n-lets repeat themselves for a clinically appropriate period of time.

In FIG. 4, each pulse train comprises four singlets in succession (with non-regular inter-pulse intervals there between); followed by four doublets in succession (with non-regular inter-doublet pulse intervals there between and non-regular inter-pulse intervals within each n-let); followed by a singlet, three doublets, and a singlet (with non-regular inter-pulse intervals there between and non-regular inter-pulse intervals within each n-let). The temporal pattern of this pulse train repeats itself in succession for a clinically appropriate period of time. The non-regular temporal pulse pattern shown in FIG. 4 has an average frequency of 67.82 Hz without loss of efficacy, as is demonstrated in the following Example, Batch 17.

In FIG. 5, each pulse train comprises four singlets in succession (with non-regular inter-pulse intervals there between); followed by three doublets in succession (with non-regular inter-doublet pulse intervals there between and non-regular inter-pulse intervals within each n-let). The temporal pattern of this pulse train repeats itself in succession for a clinically appropriate period of time. The non-regular temporal pulse pattern shown in FIG. 5 has an average frequency of 87.62 Hz without loss of efficacy, as is demonstrated in the following Example, Batch 18.

The following Example illustrates a representative methodology for developing and identifying candidate non-regular stimulation trains as shown in FIGS. 3 to 5 that achieve comparable or better efficacy at a lower average frequency (i.e., more efficiency) than constant inter-pulse interval trains.

EXAMPLE

Computational models of thalamic DBS (McIntyre et al. 2004, Birdno, 2009) and subthalamic DBS (Rubin and Terman, 2004) can be used with genetic-algorithm-based optimization (Davis, 1991) (GA) to design non-regular stimulation patterns or trains that produce desired relief of symptoms with a lower average stimulation frequency than regular, high-rate stimulation. McIntyre et al. 2004, Birdno, 2009; Rubin and Terman, 2004; and Davis, 1991 are incorporated herein by reference.

In the GA implementation, the stimulus train (pattern) is the chromosome of the organism, and each gene in the chromosome is the IPI between two successive pulses in the train. The implementation can start, e.g., with trains of 21 pulses (20 genes) yielding a train length of ~400 ms (at average frequency of 50 Hz), and the 6 s trains required for stimulation are built by serial concatenation of 15 identical pulse trains. The process can start with an initial population of, e.g., 50 organisms, constituted of random IPI's drawn from a uniform distribution. At each step (generation) of the GA, the fitness of each pulse train is evaluated using either the TC or basal ganglia network model (identified above) and calculating a cost function, C. From each generation, the 10 best stimulus trains (lowest C) are selected, to be carried forward to the next generation. They will also be combined (mated) and random variations (mutations) introduced into the 40 offspring, yielding 50 trains in each generation. This process assures that the best stimulation trains (traits) are carried through to the next generation, while avoiding local minima (i.e., mating and mutations preserve genetic diversity). See Grefenstette 1986. The GA continues through successive generations until the median and minimum values of the cost function reach a plateau, and this will yield candidate trains.

The objective is to find patterns of non-constant inter-pulse interval deep brain stimulation trains that provide advantageous results, as defined by low frequency and low error rate. An error function is desirably created that assigns the output of each temporal pattern of stimulation a specific error fraction (E) based on how the voltage output of the thalamic cells correspond to the timing of the input stimulus. Using this error fraction, a cost function (C) is desirably created to minimize both frequency and error fraction, according to representative equation $C=W*E+K*f$, where C is the cost, E is the error fraction, f is the average frequency of the temporal pattern of stimulation, W is an appropriate weighting factor for the error function, and K is an appropriate weighting factor for the frequency. The weighting factors W and K allow quantitative differentiation between efficacy (E) and efficiency (f) to generate patterns of non-constant inter-pulse interval deep brain stimulation trains that provide advantageous results with lower average frequencies, compared to conventional constant frequency pulse trains.

With this cost function, the voltage output of several candidate temporal patterns of stimulation can be evaluated and the cost calculated. Temporal patterns of stimulation with a low cost can then be used to create new temporal patterns of similar features in an attempt to achieve even lower costs. In this way, new temporal patterns of stimulation can be "bred" for a set number of generations and the best temporal patterns of stimulation of each batch recorded.

Several batches of the genetic algorithm yields useful results in that they achieve lower costs than the corresponding constant frequency DBS waveforms. Some batches can be run in an attempt to find especially low frequency temporal patterns of stimulation, by changing the cost function to weight frequency more heavily, or vice versa (i.e., by changing W and/or K). These batches can also yield lower cost results than the constant-frequency waveforms.

By way of example, a total of 14 batches of the genetic algorithm were run and evaluated with various cost functions and modified initial parameters.

Figure 6:
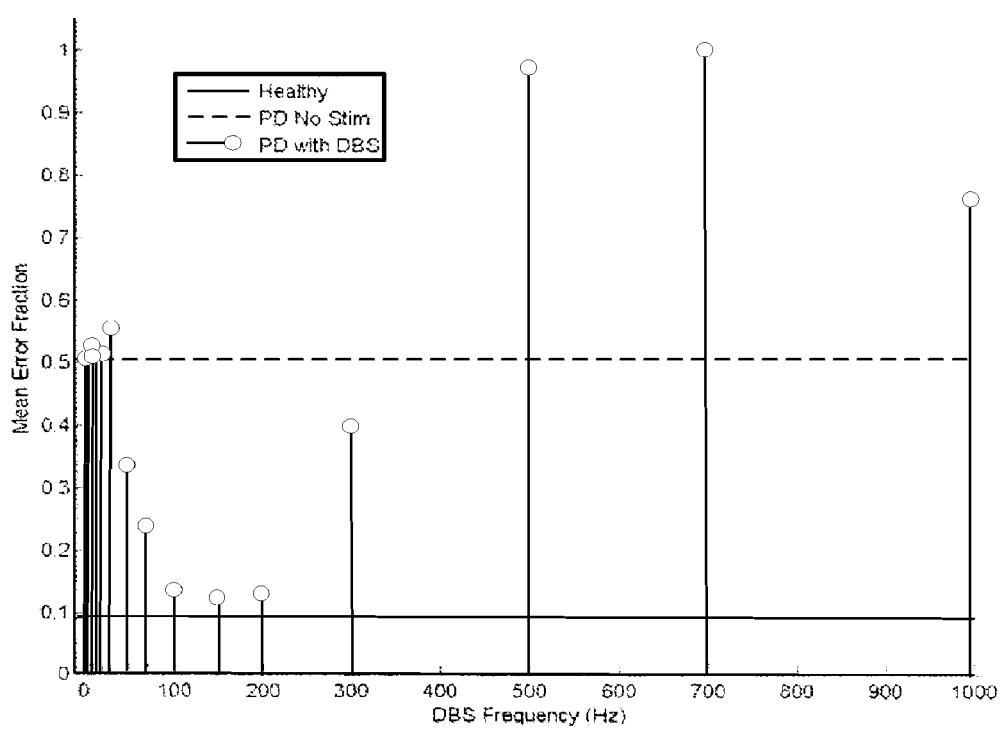
FIG. 6 is a reproduction of Example FIG. 1, as described below.

Before the trials were run, a baseline was established by running constant-frequency patterns of stimulation through the model and analyzing the associated error fractions (Example FIG. 1). As can be seen from Example FIG. 1 (FIG. 6), the healthy condition produced a low error fraction of 0.1 while the Parkinsonian condition without DBS yielded a higher error fraction of 0.5. From these results, constant high-frequency patterns of stimulation ranging from 100-200 Hz gave near perfect results. Novel non-constant temporal patterns of stimulation would then be considered advantageous if they showed error fractions very close to 0.1 with average frequencies less than 100-200 Hz.

Figure 7:
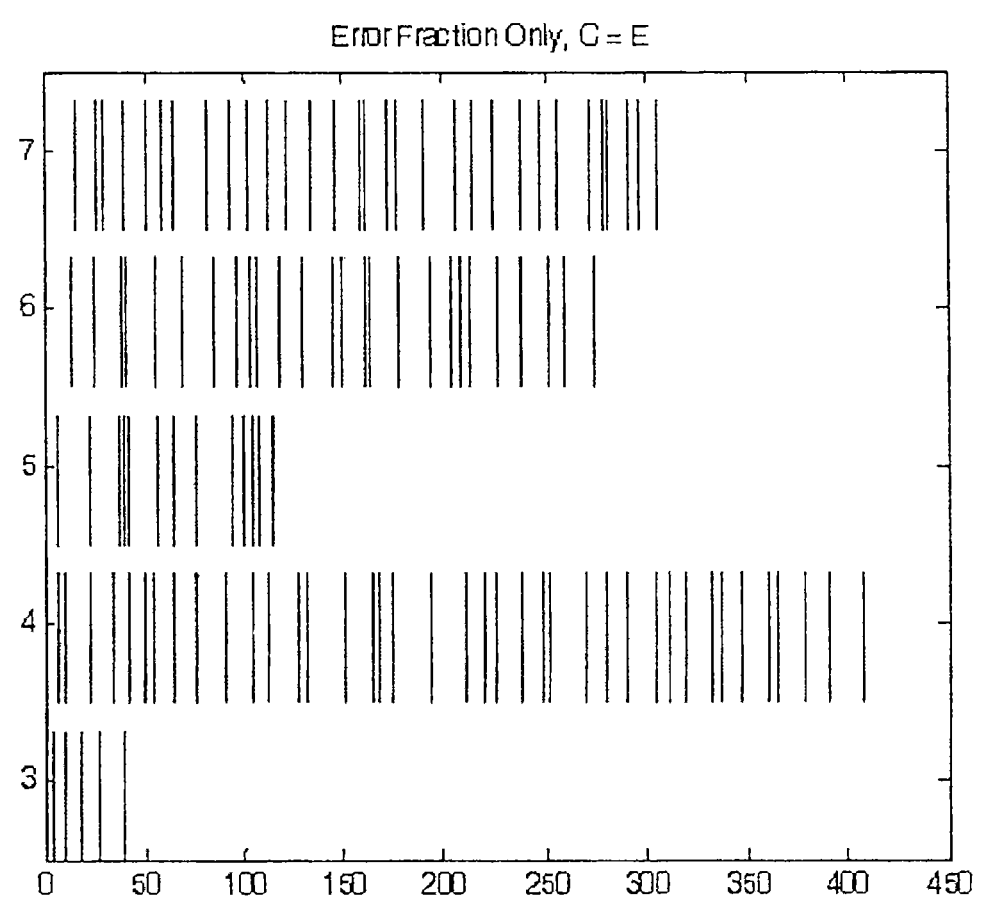
FIG. 7 is a reproduction of Example FIG. 2, as described below.
Figure 8:
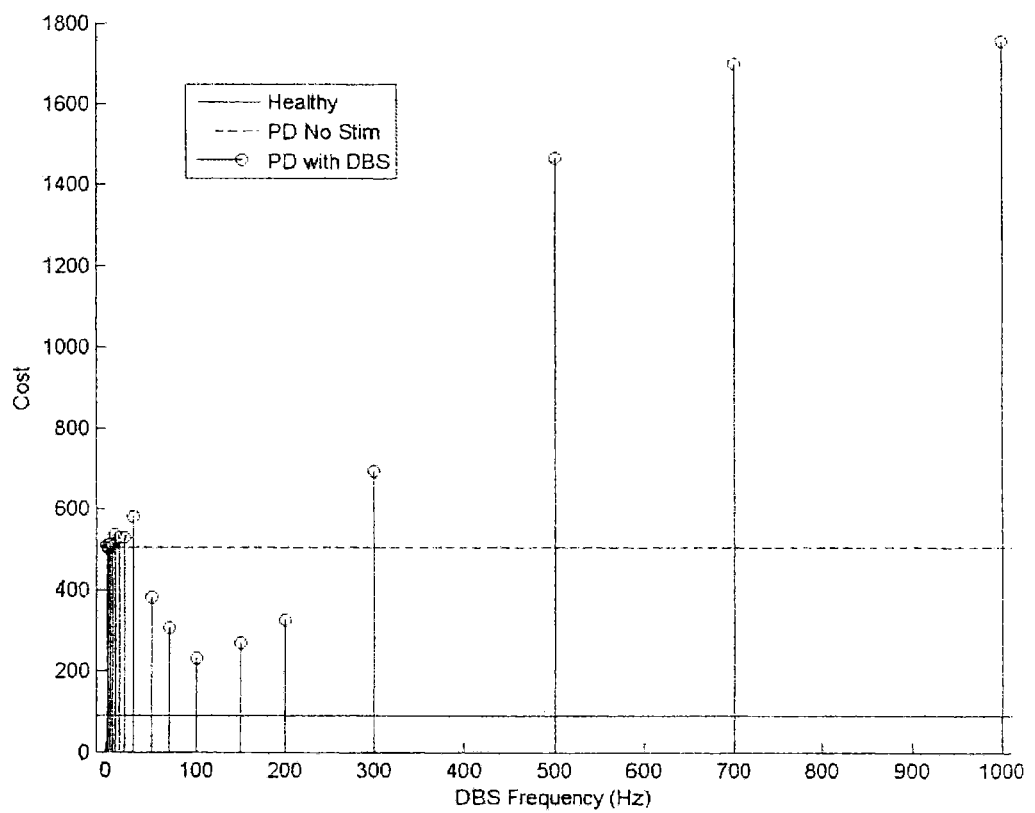
FIG. 8 is a reproduction of Example FIG. 3, as described below.

The first set of batches was run by minimizing only the error fraction (E). Thus, the associated cost function was simply C=E. The results are summarized according to average frequency and error fraction (Example Table 1). The associated inter-pulse intervals (IPI's) can be seen in Example FIG. 2 (FIG. 7). Batch 3 outputted an error fraction 0.054. Another feature is that the IPI's in Batch 3 gradually increased until about 40 msec, and then repeated itself. This provides support that ramp trains are advantageous. The trace shown in FIG. 3 generally incorporates the temporal features of Batch 3.

The remaining batches yielded error fractions higher than 0.1 and were no better than the 150 Hz constant-frequency case.

EXAMPLE TABLE 1

Error Fraction Only, C = E

| # | Average Frequency | Error Fraction | IPI Length |
|---|---|---|---|
| 3 | 127.5 | 0.054 | 5 |
| 4 | 95.62 | 0.162 | 39 |
| 5 | 113.6 | 0.139 | 13 |
| 6 | 94.64 | 0.132 | 26 |
| 7 | 101.6 | 0.142 | 31 |

Because many batches were yielding error fractions above 0.1 (healthy condition), and only a small window of error fraction less than the 150 Hz DBS case would be useful, a new cost function was constructed to minimize an alternate feature of the temporal patterns of stimulation; namely, frequency. This new cost function weighted the error fraction and frequency, yielding the equation C=1000*E+F, where C is cost, E is error fraction, and F is the average frequency of the waveform in Hz, W=1000, and K=1.

In order to establish a new baseline cost, the constant-frequency patterns of stimulation were evaluated again according to the new cost function (Example FIG. 3-FIG. 8). As can be seen from the graph, the healthy condition reported a cost of 90.65 and the Parkinson case with no DBS yielded 505.50. The best constant-frequency pattern of stimulation with the new cost function was the 100 Hz case with a cost of 231.11. This new cost function allowed for a wider range of solutions, because a temporal pattern of stimulation would be considered useful if it had a cost less than 231.11 but presumably higher than 90.65.

Figure 9:
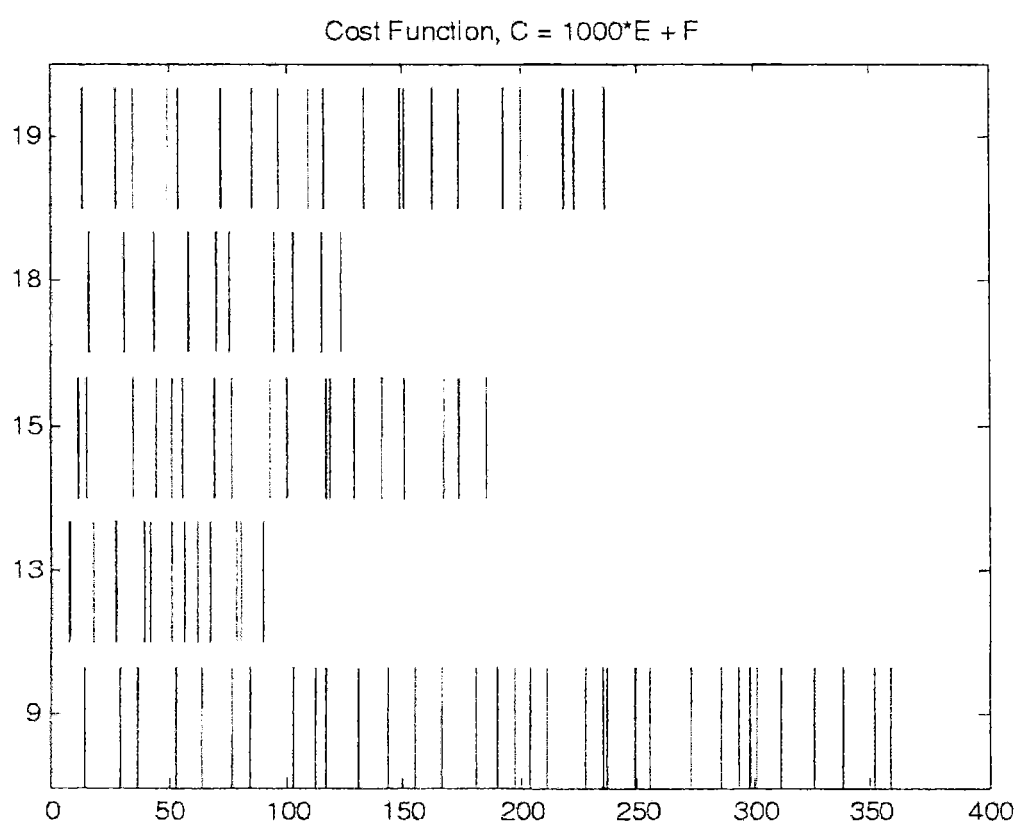
FIG. 9 is a reproduction of Example FIG. 4, as described below.

The results of the new cost function can be seen in Example Table 2 and the IPI's visualized in Example FIG. 4 (FIG. 9). The best results were seen in batches 15 and 18, which had the lowest costs. Batch 18 also exhibits a ramp-like pattern of increasing interpulse intervals. It shows a steadily falling IPI, followed by a sudden rise, and then a quick fall, rise, and fall—almost as if it consists of 3 smaller ramps. The trace shown in FIG. 5 generally incorporates the temporal features of Batch 18. Batch 15 also performed very well, but its qualitative features are more difficult to discern.

EXAMPLE TABLE 2

Cost Function, C = 1000 * E + F

| # | Average Frequency | IPI Length | Error Fraction | Cost |
|---|---|---|---|---|
| 9 | 94.74 | 34 | 0.124 | 218.8 |
| 13 | 132.9 | 12 | 0.087 | 219.4 |
| 15 | 98.00 | 17 | 0.098 | 196.0 |
| 18 | 81.28 | 10 | 0.116 | 197.3 |
| 19 | 84.70 | 20 | 0.116 | 201.2 |

The advantage of low frequency was emphasized with a new cost function, which weighted frequency more heavily, C=1000*E+2*F. Because the frequency of DBS does not affect the healthy condition or the PD with no DBS, these baseline costs stayed the same at 90.65 and 505.50, respectively. The 100 Hz was again the best constant-frequency temporal pattern of stimulation, with a cost of 331.11. The following temporal patterns of stimulation, then, were considered useful if they had low frequencies and costs less than 331.11 and greater than 90.65.

Figure 10:
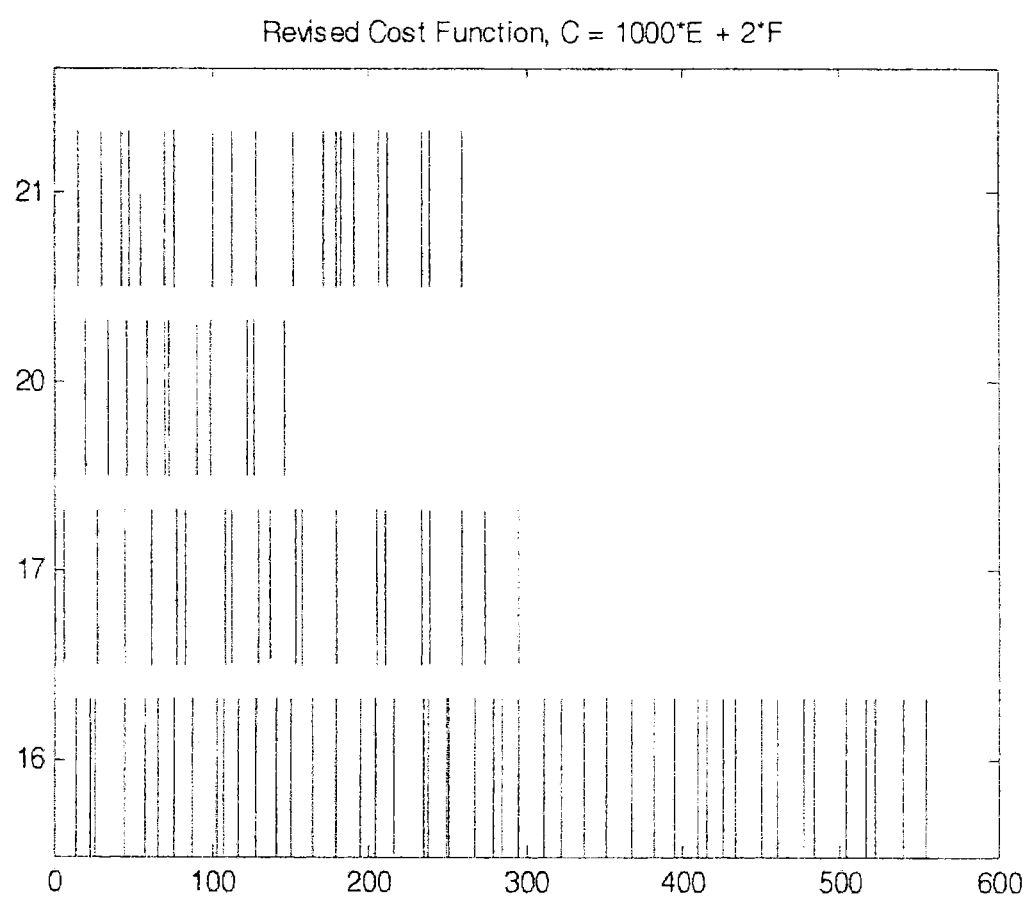
FIG. 10 is a reproduction of Example FIG. 5, as described below.

The results of the revised cost function can be seen in Example Table 3 and the IPI's visualized in Example FIG. 5 (FIG. 10). Of the resulting batches, batch 17 proved most interesting because of its very low average frequency of 67.82 Hz. Even with such a low frequency, it managed to prove better than the 100 Hz condition with a reduction in cost of about 10. The waveform of batch 17 is interesting in that it consists of a ramp pattern of decreasing IPI in the first 100 msec, followed by a continual shift between large IPI and small IPI. The qualitative feature of quickly changing between large and small IPI's may prove advantageous. The trace shown in FIG. 4 generally incorporates the temporal features of Batch 17.

EXAMPLE TABLE 3

Revised Cost Function, Cost = 1000 * E + 2 * F

| # | Average Frequency | IPI Length | Error Fraction | Cost |
|---|---|---|---|---|
| 16 | 84.92 | 47 | 0.239 | 323.8 |
| 17 | 67.82 | 20 | 0.253 | 321.1 |
| 20 | 79.25 | 10 | 0.236 | 315.4 |
| 21 | 77.15 | 20 | 0.269 | 346.6 |

The most interesting temporal patterns of stimulation in this Example are from batches 15, 17, and 18. Batch 15 produced a temporal pattern of stimulation with an average frequency of 98 Hz with an error fraction as low as 0.098. Thus, it outperformed the 100 Hz constant-frequency case by managing to lower the error even further at roughly the same frequency. Still, the qualitatively useful features of batch 15 are difficult to discern. Batch 17 was also appealing because of its very low frequency of 67.82. This low frequency was gained at the cost of increased error at 0.253, but it may nonetheless be useful if emphasis is placed on maintaining low frequency DBS. The qualitative features of batch 17 indicated at first a ramp followed by a continual switching between low and high IPI's. Lastly, batch 18 stood somewhere in the middle with a fairly low frequency of 87.62 and low error fraction of 0.116, only marginally higher than the healthy condition of 0.1. The dominant qualitative feature of batch 18's waveform is that it too shows a ramp nature in that the IPI initially steadily falls, then quickly rises, falls, and then rises. The rapid changing between high and low IPI of batch 17 can be envisioned as a set of steep ramps.

A comparison of Batch 17 (FIG. 4) and Batch 18 (FIG. 5) demonstrates how the balance between efficacy (as a function of the model error fraction E) and efficiency (as a function of frequency f) in non-regular temporal patterns of stimulation can be purposefully tailored to meet clinical objectives. The systems and methodologies discussed allow changing the cost function by weighting efficacy or frequency more heavily (i.e., by changing W and/or K), while still yielding temporal patterns of stimulation with lower cost results than the constant-frequency waveforms. Comparing Batch 17 with Batch 18, one sees that the error fraction (E) (i.e., the efficacy of the temporal pattern) of Batch 17 (0.253) is greater than the error fraction (E) (i.e., the efficacy of the temporal pattern) of Batch 18 (0.116). However, one can also see that the efficiency (i.e., the average frequency) of Batch 17 (67.82 Hz) is lower than the efficiency (i.e., the average frequency) of Batch 18 (81.28 Hz). Through different in terms of efficacy and efficiency, both Batch 17 and Batch 18 have costs better than constant-frequency temporal patterns.

Figure 11:
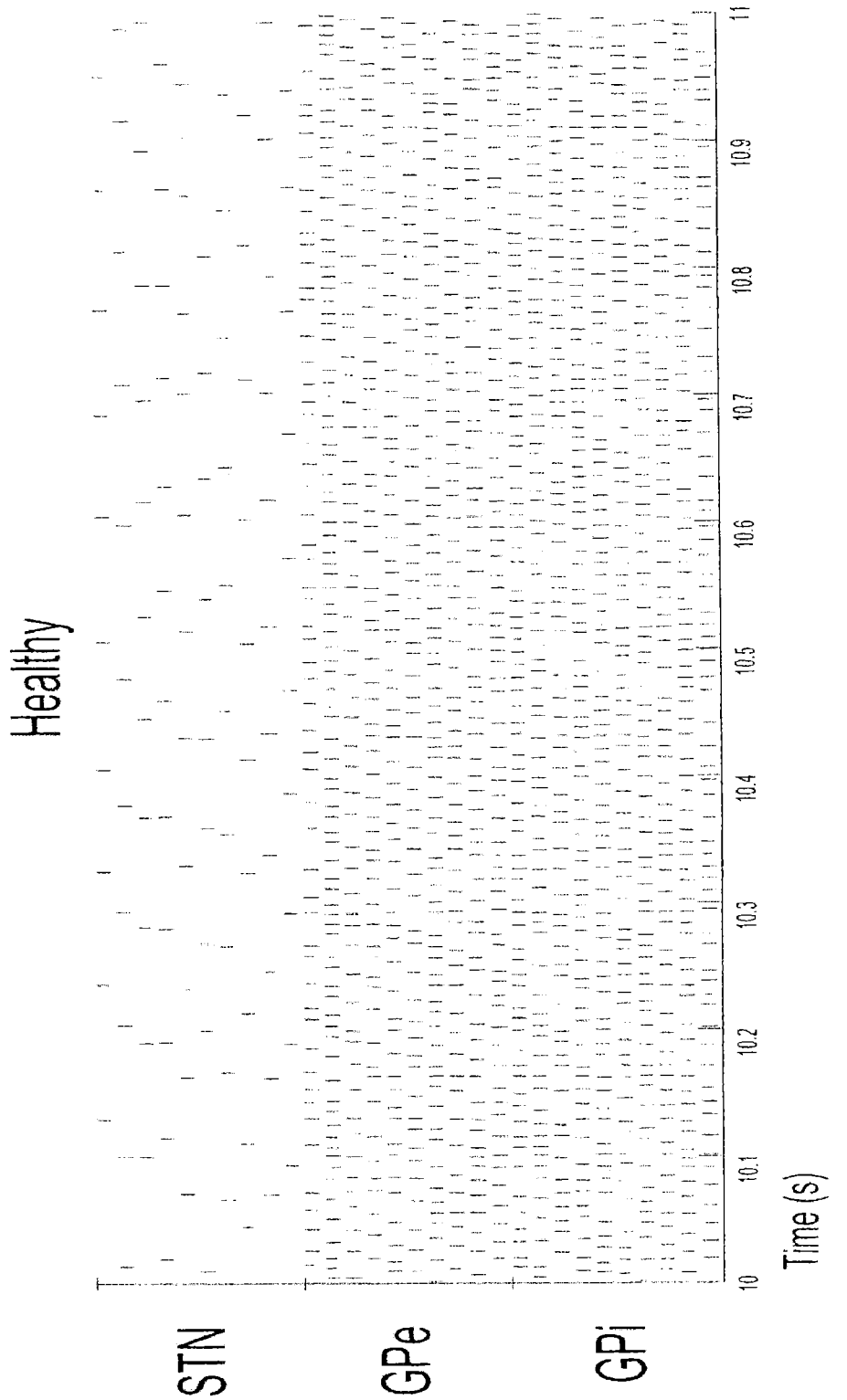
FIG. 11 is a raster of the neuronal firings of ten neurons in each of the subthalamic nucleus, the global pallidus exterior, and the global pallidus interior, generated by a computer model of a healthy human.

FIG. 11 depicts a modeled raster of healthy firing of neurons in the subthalamic nucleus and the global pallidus, both external and internal segments thereof, through about one second of time.

Figure 12:
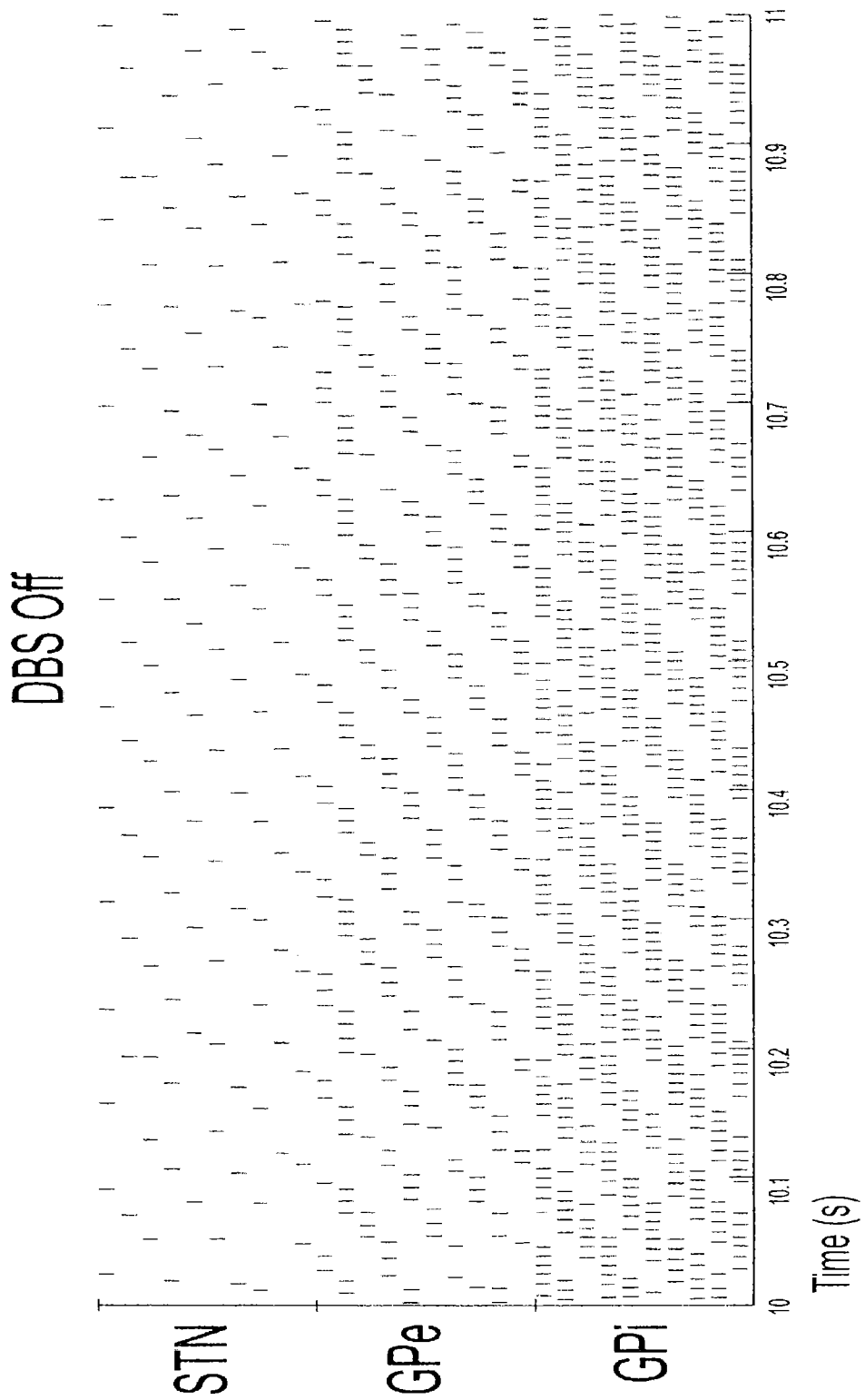
FIG. 12 is a raster of the neuronal firings of ten neurons in each of the subthalamic nucleus, the global pallidus exterior, and the global pallidus interior, generated by a computer model of a human having a neurological condition, such as Parkinson's Disease.

FIG. 12 depicts a modeled raster of the healthy subject modeled in FIG. 11, with the addition of a forced Parkinsonian state, however with deep brain stimulation not being applied to the model. Like the raster of FIG. 11, this Figure depicts neurons in the subthalamic nucleus and the global pallidus, both external and internal segments thereof, through about one second of time.

Figure 13:
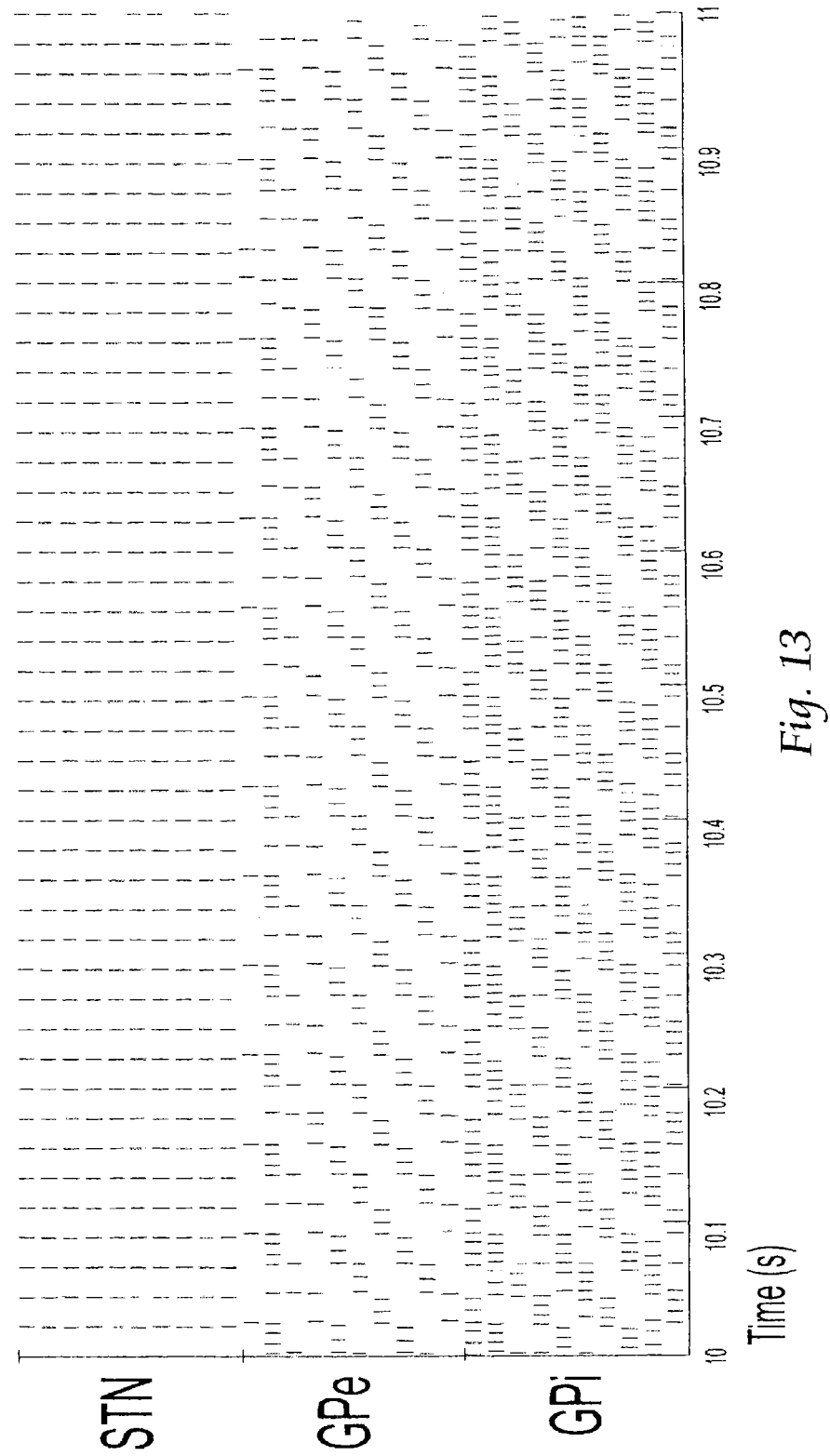
FIG. 13 is a raster of the neuronal firings of ten neurons in each of the subthalamic nucleus, the global pallidus exterior, and the global pallidus interior, generated by a computer model of an electrical deep brain stimulation of regular interval applied to the subthalamic nucleus at 45 Hertz.

FIG. 13 depicts a modeled raster of the modeled Parkinsonian subject of FIG. 12, however further applying a regular 45 Hz regular interval DBS signal to the subthalamic nucleus, as can be seen. Additionally, the figure shows the firing of neurons in the global pallidus, both external and internal segments thereof, through about one second of time.

Figure 14:
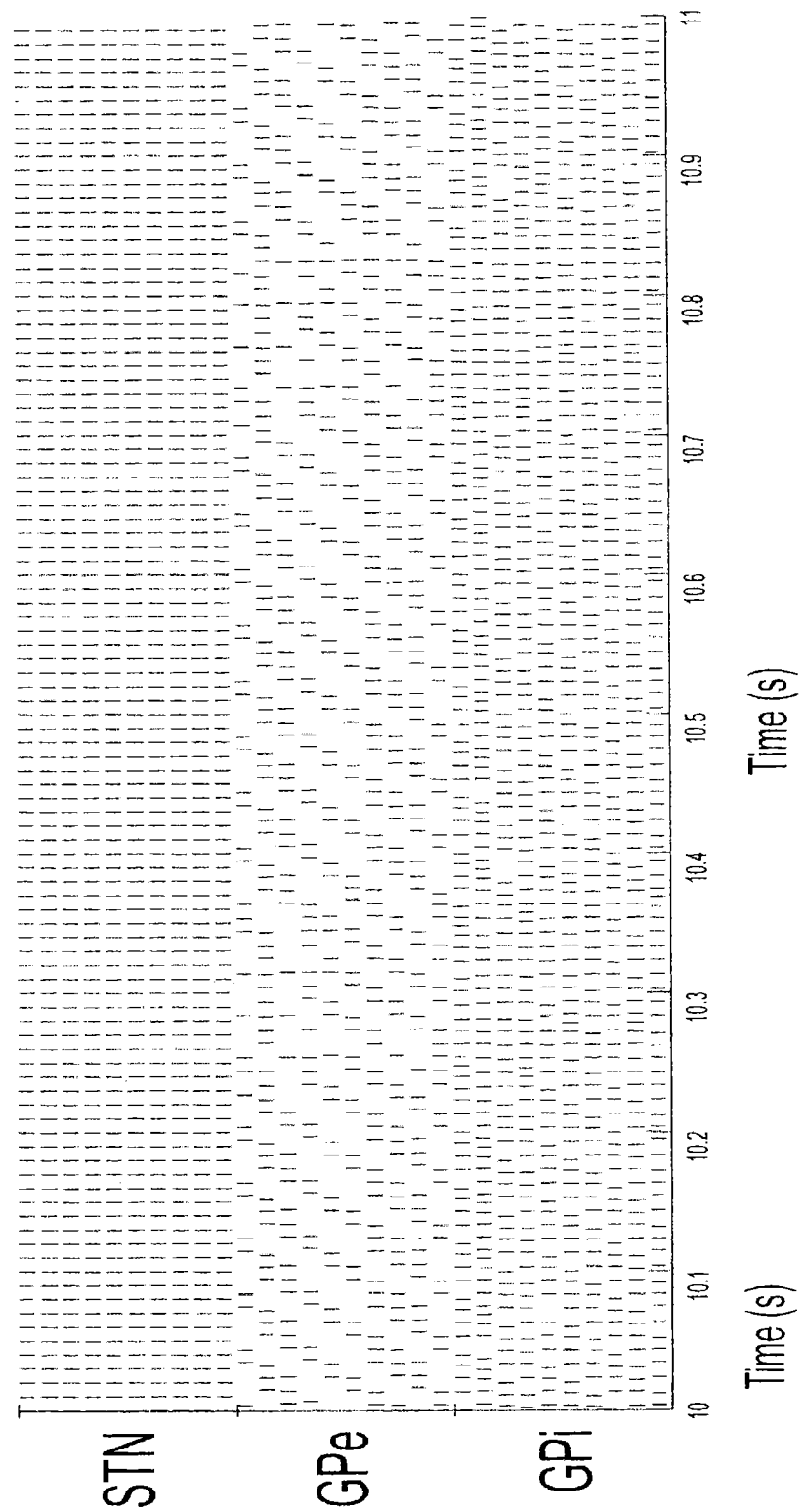
FIG. 14 is a raster of the neuronal firings of ten neurons in each of the subthalamic nucleus, the global pallidus exterior, and the global pallidus interior, generated by a computer model of an electrical deep brain stimulation of regular interval applied to the subthalamic nucleus at 100 Hertz.

FIG. 14 depicts a modeled raster of the modeled Parkinsonian subject of FIG. 12, however further applying a regular 100 Hz regular interval DBS signal to the subthalamic nucleus, as can be seen. Additionally, the figure shows the firing of neurons in the global pallidus, both external and internal segments thereof, through about one second of time.

Figure 15:
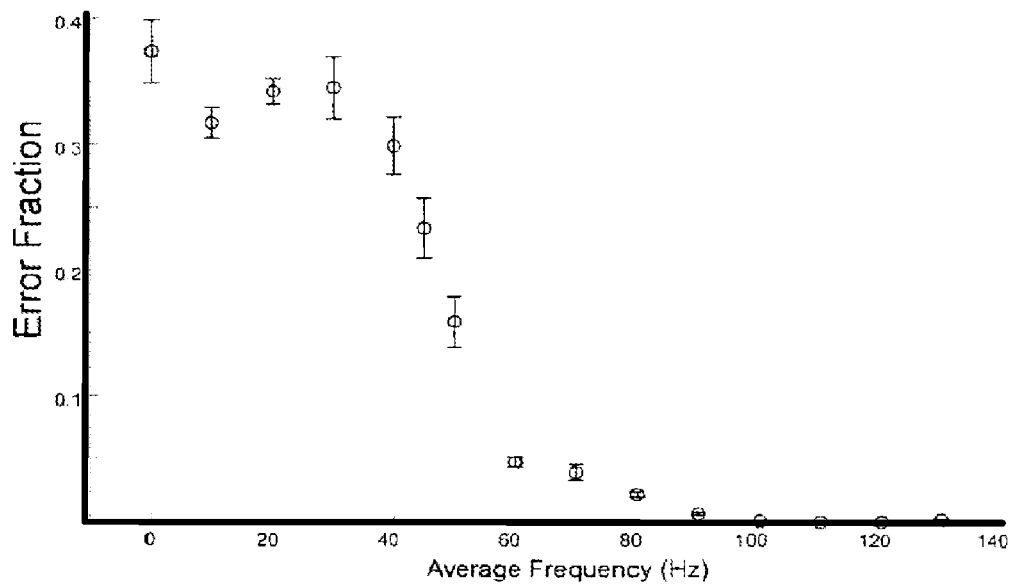
FIG. 15 is a plot of a computer-generated error fraction of a regular interval electrical DBS applied at the given average frequency.

FIG. 15 depicts a graphical representation of modeled, conventionally expected error fractions where a regular interval DBS signal is applied to the Parkinsonian model. The goal in determining optimum stimulation patterns may be to provide a stimulation pattern that has a lower average frequency with at least as good, if not better (lower) error fractions than regular interval DBS signals presented to the STN. By way of a non-limiting example, with DBS off (average frequency=0 Hz), the model provides that an expected error fraction may be about 0.34 to about 0.40. With a regular interval stimulation pattern applied to the STN at about 45 Hz, the expected error fraction is about 0.20 to about 0.25. According to the model, and therefore generally accepted in the field, higher average frequency regular interval stimulation yields a lower error fraction. Accordingly, if stimulation could be provided at an average frequency of about 45 Hz with a modeled error fraction less than that expected (i.e., less than about 0.20), benefits would be realized. Not only would relief from brain disorders be improved, but power consumption by any device delivering the new stimulation patterns, would be reduced as compared to the same device delivering regular interval stimulation patterns in an attempt to achieve similar performance results.

Figure 16:
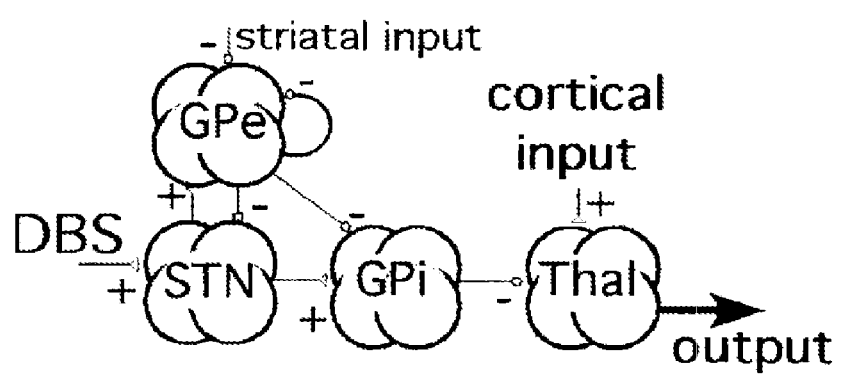
FIG. 16 diagrammatically illustrates an embodiment of a computer model that may be used to analyze and generate embodiments stimulation patterns according to the present invention.

FIG. 16 provides an illustration of a model structure that may be used to generate stimulation patterns according to the present invention. Reference to this illustration may be helpful in explaining what is referred to herein as an "error fraction." As used herein, an "error fraction" is generally understood to mean the number of errors occurring at the output of a model as compared to the number of inputs provided to the model. An output error occurs when a contrast arises between an expected value of the model output to an output generated by the model provided with a given stimulation pattern, such as to the STN, as shown.

Figure 17:
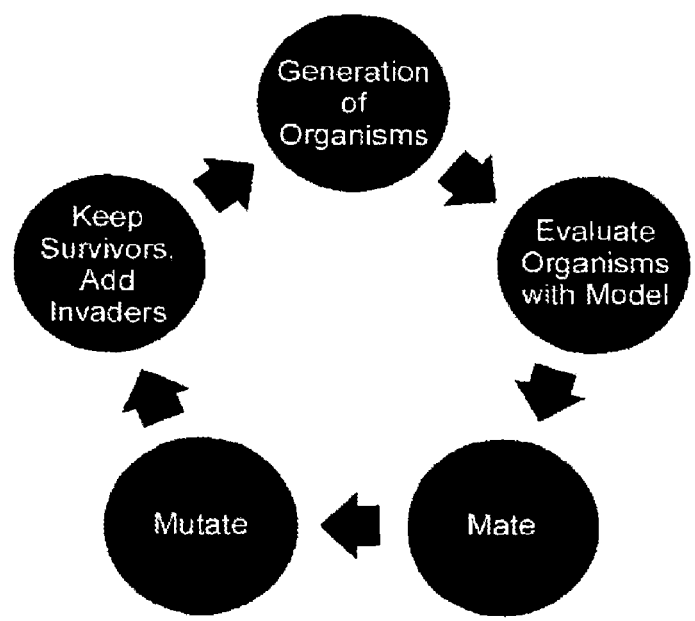
FIG. 17 is a diagram of a general genetic algorithm process.
Figure 18:
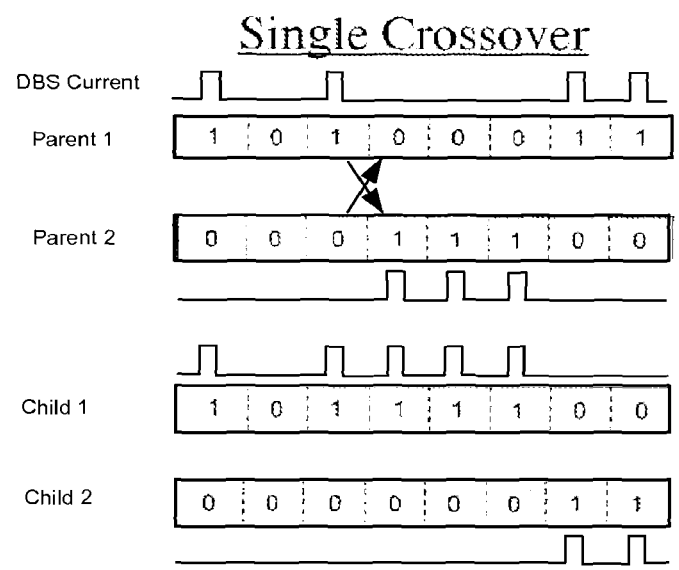
FIG. 18 is an embodiment of a generational crossover of stimulation patterns according to the present invention.

FIG. 17 generally depicts a known genetic algorithm process model, beginning with the generation of organisms (in this case pulse trains or stimulation patterns), and continuing as described above. One method for a mating process that may be employed in the genetic algorithm according to the present invention is a single crossover process by which certain, but preferably not all, genes (stimulation pulses) are exchanged between parent stimulation trains so as to yield two child stimulation trains are generated. As depicted in FIG. 18, the stimulation patterns include a series of 1's and 0's, which indicate whether or not, respectively, a stimulation pulse is to be delivered during a given time step, such as about 500 microseconds to about 100 milliseconds, and preferably about one to 5 milliseconds. While initial or starting stimulation patterns may be created by drawing interpulse intervals from some distribution, such as a Gaussian distribution, the initial stimulation patterns are preferably generated randomly, and constraints may be added to control the number of stimulation pulses (1's) in the initial stimulation patterns, thereby controlling the average frequency range of the stimulation pattern. Resulting generational stimulation patterns are then evaluated by the model and compared to the performance of regular interval stimulation patterns provided to the model at the same average frequency as the generational stimulation pattern currently under evaluation.

Figure 19:
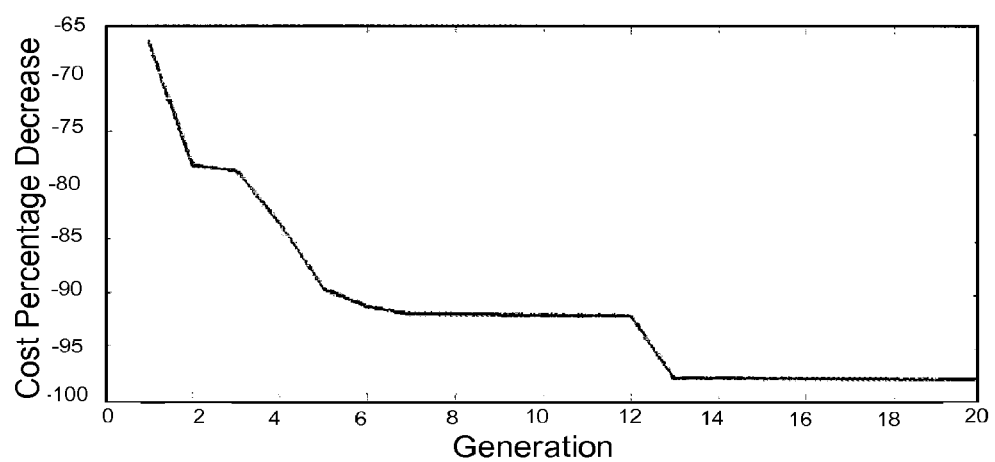
FIG. 19 is a plot of a percent decrease cost function versus the number of generations run in an evolutionary algorithm according to the present invention.

Another cost function that has proven useful in determining beneficial non-regular temporal patterns of stimulation generated by a genetic algorithm is as follows: $C=(E_{GA}-E_{FMReg})/E_{FMReg}*100\%$ where $E_{GA}$ is the error fraction of a selected generational stimulation pattern generated by the genetic algorithm and currently under analysis by the model and $E_{FMReg}$ is the error fraction of a DBS stimulation pattern of uniform frequency at a frequency equal to the average frequency of the GA train under analysis. This may be referred to generally as a percent change cost function. At first, one might expect that this cost function would not force a genetic algorithm to search for non-regular patterns of DBS with a low average frequency. However, this is not the case; the GA is inclined to search for non-regular stimulation pattern of DBS with a low average frequency because there is a greater opportunity to find improved stimulation patterns (i.e., having a lower error fraction) at lower frequencies. That is, as shown in FIG. 15, the error fraction associated with 130 Hz conventional regular-interval DBS is already so close to zero that it is highly unlikely that a non-regular pattern with an average frequency of 130 Hz is going to have a smaller error fraction. In other words, there just is not much room to improve at 130 Hz. On the other hand, at 45 Hz, there is ample room for improvement. It is much more likely that a non-regular pattern of DBS with an average frequency of 45 Hz will be found that has a better performance than conventional regular-interval DBS provided at 45 Hz. Therefore, using a percent decrease cost function implicitly incorporates the average frequency of DBS while helping to minimize complications of selecting weighting parameters, as with the other cost functions discussed herein. As shown in FIG. 19, it is beneficial to run the genetic algorithm through a plurality of generations so as to decrease the cost. This figure shows the (decline in) cost as the genetic algorithm progresses. That is, the algorithm is identifying better and better stimulation patterns, from generation to generation, and subsequently the cost is declining, or, in other words, the performance is increasing.

Figure 20:
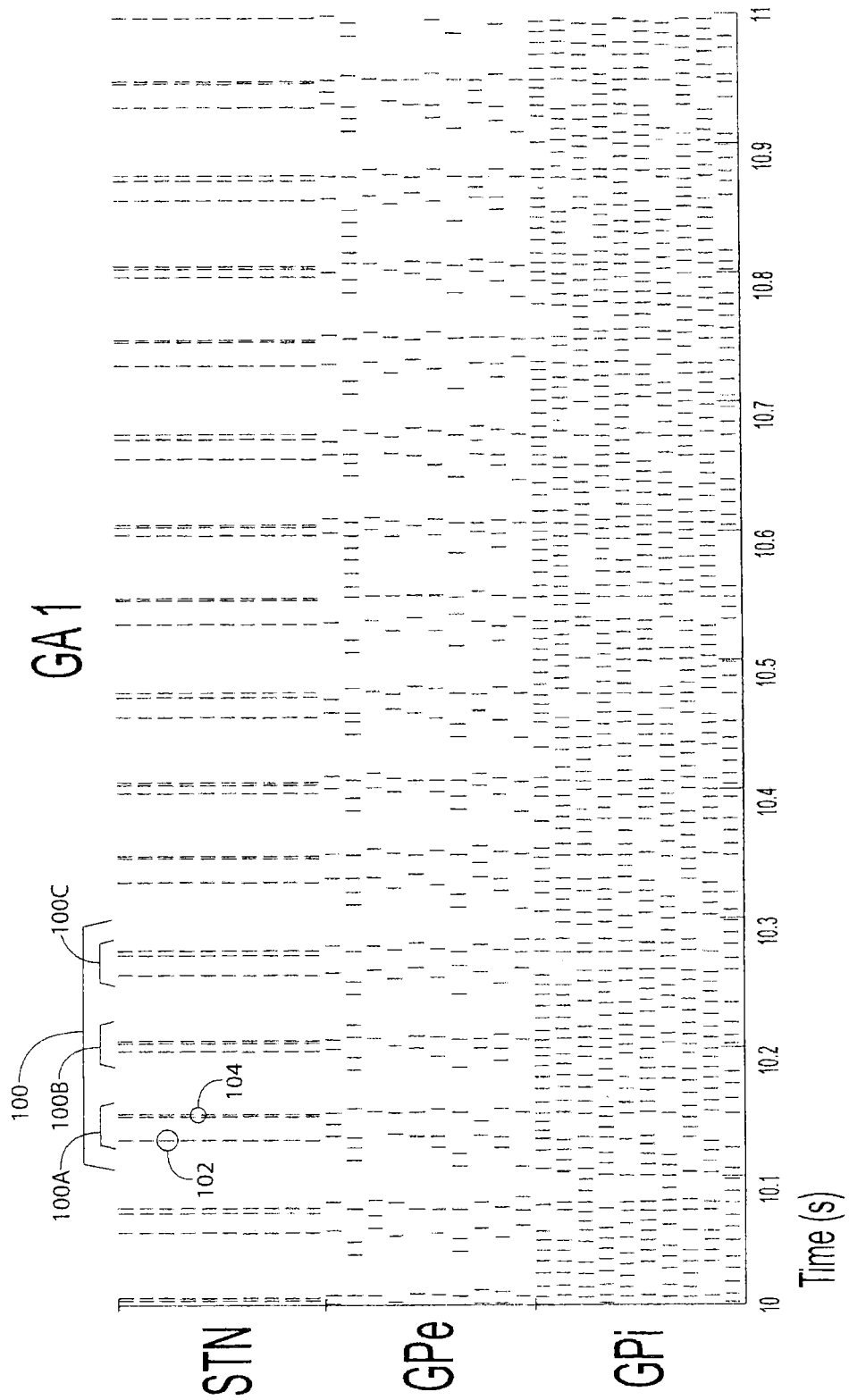
FIG. 20 is a raster of the neuronal firings of ten neurons in each of the subthalamic nucleus, the global pallidus exterior, and the global pallidus interior, generated by a computer model of an electrical deep brain stimulation applied to the subthalamic nucleus according to a first embodiment of a stimulation pattern according to the present invention.
Figure 21:
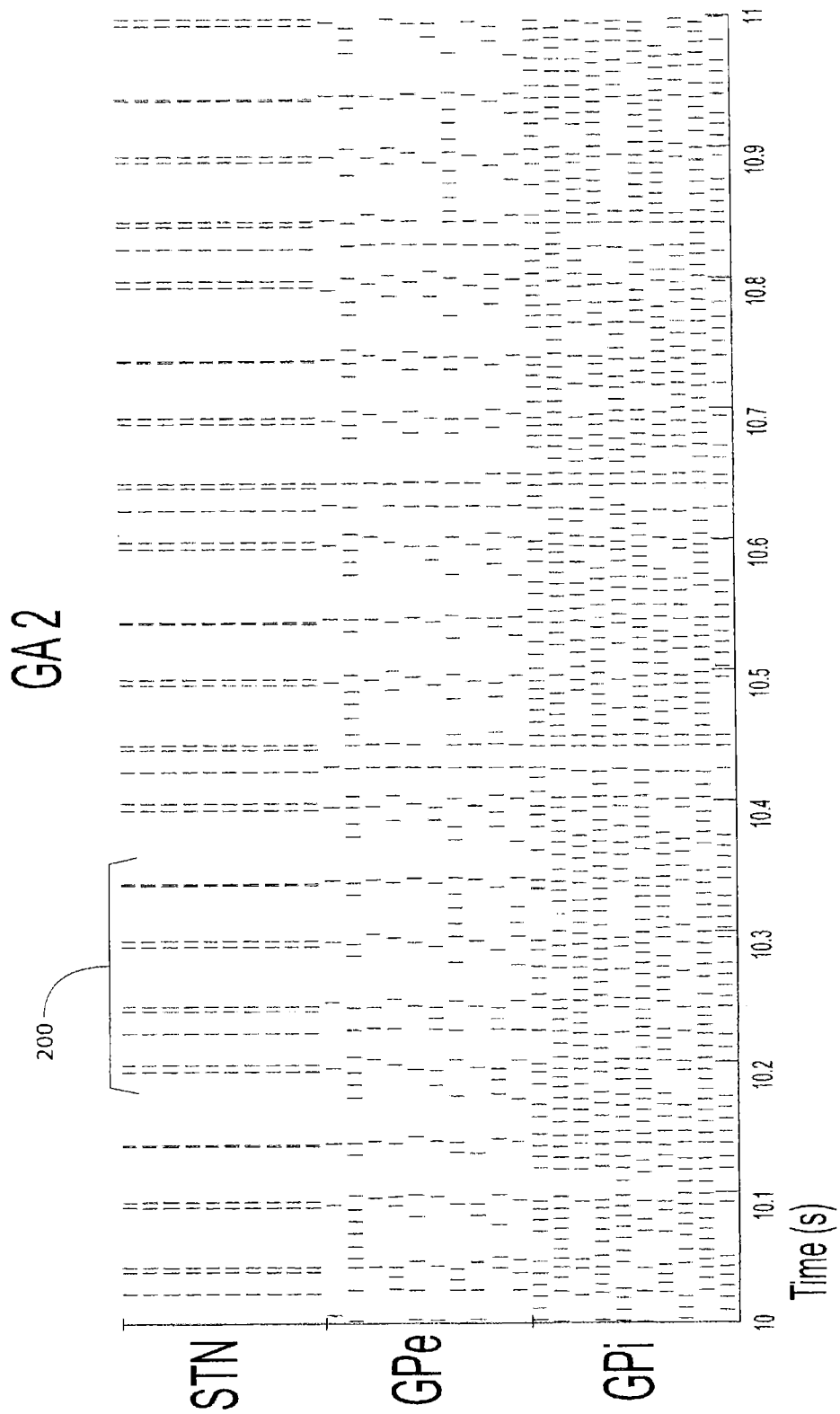
FIG. 21 is a raster of the neuronal firings of ten neurons in each of the subthalamic nucleus, the global pallidus exterior, and the global pallidus interior, generated by a computer model of an electrical deep brain stimulation applied to the subthalamic nucleus according to a second embodiment of a stimulation pattern according to the present invention.
Figure 22:
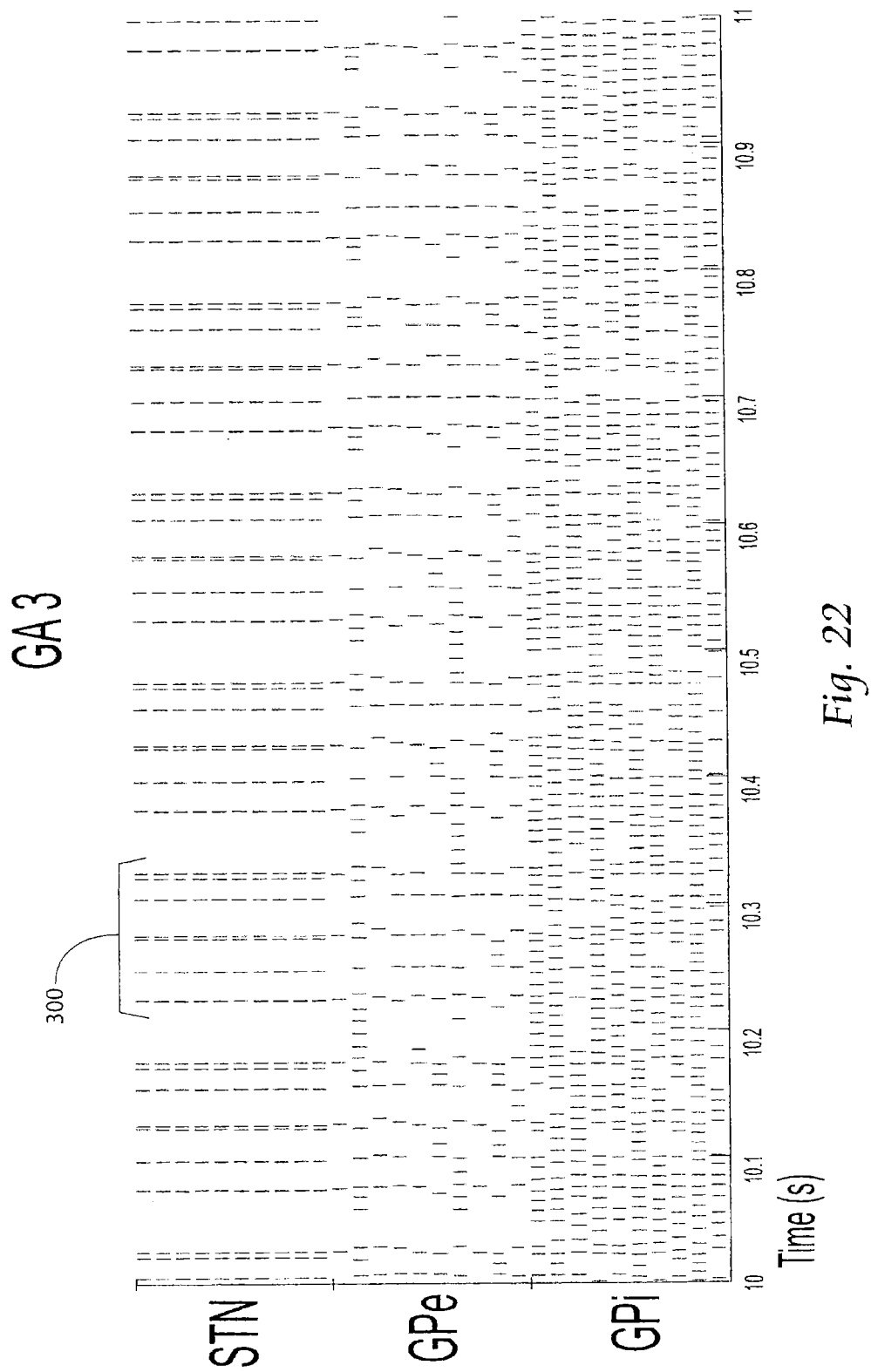
FIG. 22 is a raster of the neuronal firings of ten neurons in each of the subthalamic nucleus, the global pallidus exterior, and the global pallidus interior, generated by a computer model of an electrical deep brain stimulation applied to the subthalamic nucleus according to a third embodiment of a stimulation pattern according to the present invention.

Three stimulation trains generated according to the present invention utilizing the percent change cost function to guide survival and propagation are shown in FIGS. 20-22. In FIG. 20, a preferred GA1 stimulation train is shown as being applied to the STN of a Parkinsonion brain model. The preferred stimulation pattern includes the repetition of a set 100 of three triplet stimulation pulses 100A, 100B, 100C, where each triplet preferably comprises a singlet 102 followed by a doublet 104. Through any given set 100 of triplets, the interpulse interval between the singlet and doublet of one triplet is preferably different than the interpulse interval between the singlet and doublet of at least one other triplet, and more preferably different than each interpulse interval between the singlet and doublet of all other triplets in the set 100. Furthermore, the interpulse interval within the doublets of each triplet is preferably different than at least one other doublet interpulse interval within that set 100, and more preferably the interpulse interval within each doublet in a given set 100 is different than the interpulse interval within each other doublet in that set 100. While the interpulse intervals between the singlets and doublets of a given set, and within the doublets of the given set, may vary (as much as integer factors), the interpulse interval between each triplet within a given set preferably remains relatively constant, such as by varying less than about 10% throughout the set.

In each of the described preferred stimulation patterns, a given set to be repeated includes at least one doublet and at least one singlet. As in the case of the GA1 train, the number of singlets and doublets in a given set 100 was equal (three of each). As in the case of the GA2 pattern set 200, as shown in FIG. 21, the number of doublets far outweighed the number of singlets (80% of n-lets were doublets as opposed to 20% as singlets). As in the case of the GA3 pattern set 300, as shown in FIG. 22, the number of doublets outweighed the number of singlets (60% of n-lets were doublets as opposed to 40% as singlets). Accordingly, it may be more preferable to include, in a given stimulation pattern to be repeatedly delivered to the subthalamic nucleus or other portion of the brain, one or more singlets and one or more doublets, where the number of doublets is equal to or greater than the number of singlets in the set.

Figure 23:
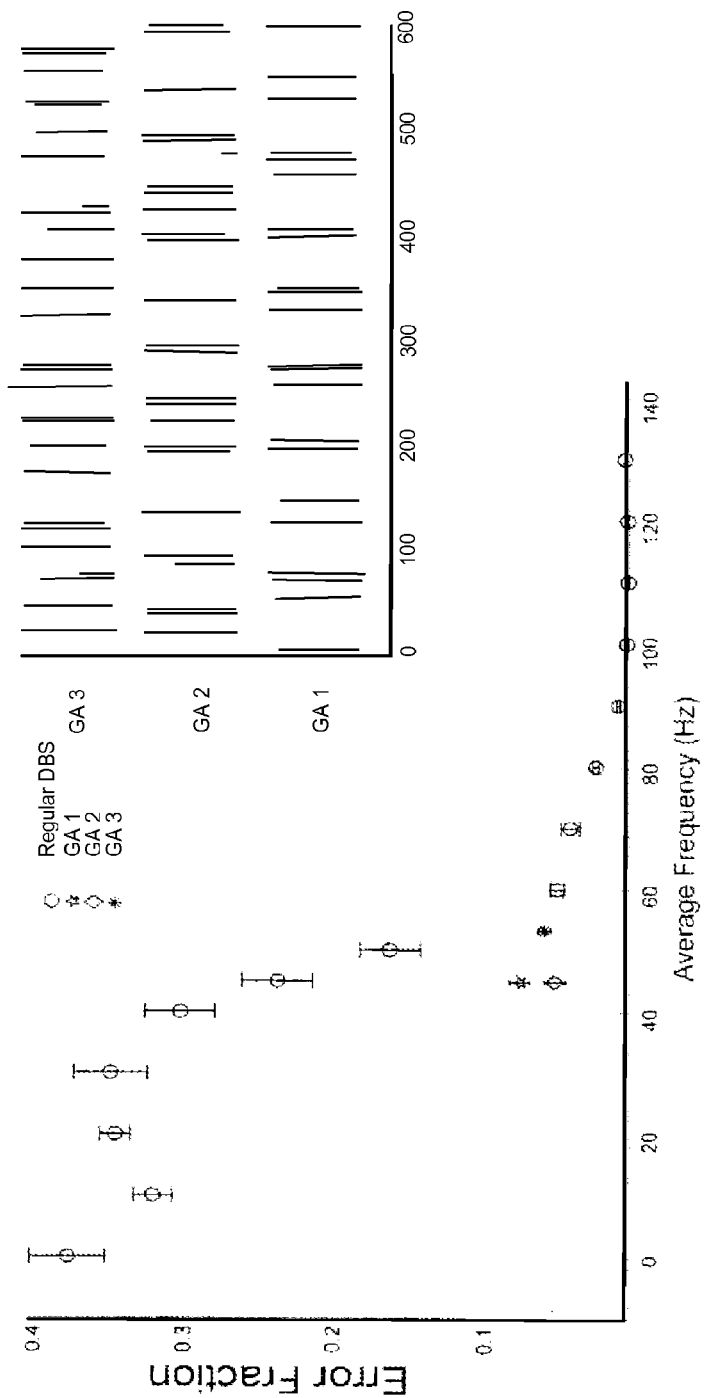
FIG. 23 is FIG. 15, further including a plot of the computer modeled error fractions generated by the use of the stimulation patterns of FIGS. 20-22.

As shown in FIG. 23, the stimulation patterns generated according to the present invention have a much lower error fraction value as compared to their regular interval stimulation counterparts at frequencies less than 100 Hz. For example, at 45 Hz, regular interval DBS has an error fraction of about 20 in 100 (0.20) to about 25 in 100 (0.25). On the other hand, the stimulation patterns generated according to the present invention provide a modeled error fraction of about 5 in 100 to about 15 in 100, thereby demonstrating a 25% to 80% improvement in efficiency.

Figure 24:
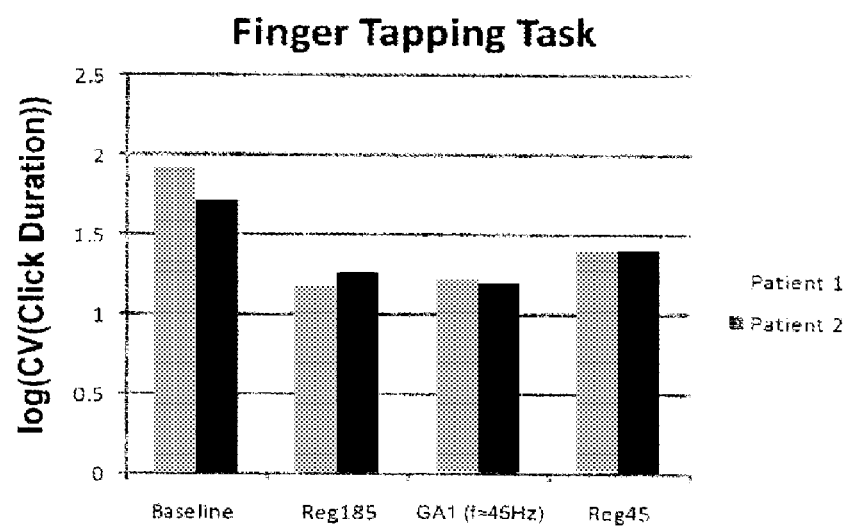
FIG. 24 is a graph of a quantitative measurement of the performance of the stimulation pattern of FIG. 20 as compared to other stimulation patterns in two human patients which had been diagnosed with Parkinson's Disease.

An electrical stimulation pattern created according to the present invention (GA1) was experimentally applied to two human patients that had been diagnosed with Parkinson's Disease. The GA1 pattern was applied during intraoperative experiments that were conducted by connecting to an exposed lead of a previously implanted DBS electrode during an implantable pulse generator replacement surgery. After connection, the GA1 pattern of stimulation and a few control patterns were delivered. Motor impairment was quantified while delivering the patterns of stimulation using a known finger-tapping task. To measure the effect of the DBS stimulation patterns according to the present invention, a two-button computer mouse was utilized, and the patient was instructed to, during data collection times, alternate clicking a respective mouse button with their index finger and their middle finger. The time duration of the respective button clicks was then recorded by a computer and analyzed. The time duration of one or both fingers may be analyzed, depending upon statistical results. As can be seen in FIG. 24, the GA1 stimulation pattern allowed each patient to demonstrate an increase in motor function as compared to the regular interval DBS stimulation pattern provided at the same average frequency, thus indicating an increased benefit in performance with no sacrifice to average cost (i.e., no increase in average power). Furthermore, for Patient 1, the GA1 stimulation pattern caused the patient to perform substantially similar to motor function demonstrated under application of a regular interval DBS stimulation pattern of 185 Hz, thus indicating substantial similar performance with a great cost (i.e. power) reduction (stimulation provided at an average of 45 Hz instead of 185 Hz). Finally, with respect to Patient 2, the GA1 stimulation pattern caused the patient to perform better than the motor function demonstrated under application of a regular interval DBS stimulation pattern of 185 Hz, thus indicating improved performance with a great cost (i.e. power) reduction (stimulation provided at an average of 45 Hz instead of 185 Hz). Generally speaking, then, the 45 Hz average frequency stimulation pattern designed according to the present invention performed similarly or better than conventional 185 Hz regular DBS stimulation and better than frequency matched (45 Hz) regular stimulation. Further clinical experiments have been conducted in applying stimulation to the STN using stimulation patterns generated according to the present invention, and such experiments show promising results.

An electrical stimulation pattern created according to the present invention (GA1) was also tested in one human subject with Parkinson's disease where tremor was that subject's primary motor symptom. The subject's tremor was quantified using as accelerometer on the back of the subject's contralateral wrist.

Figure 28A:
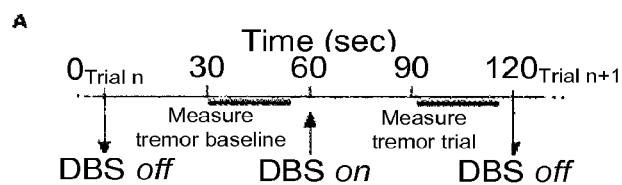
FIG. 28A is a graphical representation of a measure of an experimental tremor during a trial.

Tremor was measured in the contralateral limb during unilateral stimulation with a temporal pattern of stimulation generated according to the present invention having an average frequency of about 45 Hz, regular 45 Hz and 185 Hz stimulation, and with stimulation off (controls) in a single intraoperative session with a human subject. The stimulation pattern was presented to the subject, and the subject was blinded to the experimental condition. The trial began with one minute of stimulation off, with baseline tremor measured for 20 seconds beginning about 30 seconds into these intervals, and about 30 seconds after each condition was initiated experimental tremor was measured for 20 seconds (Ex. FIG. 28A).

Figure 28B:
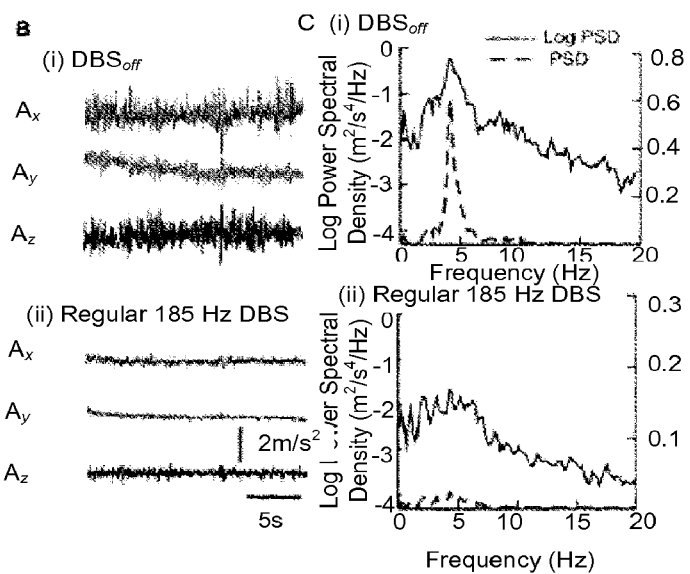
FIG. 28B is a graphical representation of amplitude of tremors with a power spectral density calculated for each of the measured amplitudes.

Tremor was measured using an accelerometer (Crossbow CXL04LP3; 5V/4 g sensitivity, San Jose, Calif., USA) taped to the dorsum of the hand. The amplitude of tremor recorded by an accelerometer generally correlates well with clinical tremor rating scales. To obtain a single quantitative measure of tremor, the power spectral density was calculated for each of the three acceleration signals (AX, AY, and AZ, Ex. FIG. 28B) using the psd function (power spectral density, Welch's averaged periodogram, Hanning window, FFT length=5, 000) in MATLAB (Mathworks Inc., Natick, Mass., USA). Next, we integrated each spectrum from 2-20 Hz to get PX, PY, and PZ. Finally, we summed PX, PY, and PZ, and took the log of the sum to get a single metric of tremor. The frequency range of 2-20 Hz was chosen to include the primary and several harmonics of the tremor and to exclude steady state acceleration due to gravity.

Figure 25:
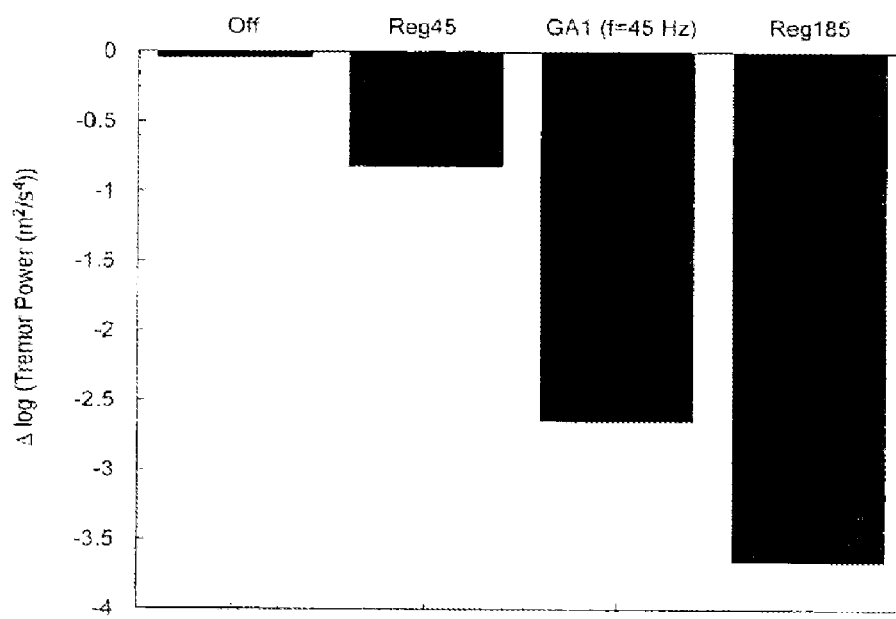
FIG. 25 is a graph of a quantitative measurement of the performance of the stimulation pattern of FIG. 20 as compared to other stimulation patterns in a human patient which had been diagnosed with Parkinson's Disease and had tremor as a primary motor impairment related thereto.

As mentioned, the power spectral density for the acceleration signal was integrated from 2-20 Hz in order to get a single quantitative measure of the tremor amplitude. As can be seen in FIG. 25, the stimulation pattern generated according the present invention having an average frequency of about 45 Hz (GA1) reduced the tremor amplitude more than the regular 45 Hz stimulation but slightly less than regular 185 Hz stimulation. All three patterns of stimulation reduced tremor amplitude compared to the stimulation off condition.

Figure 26:
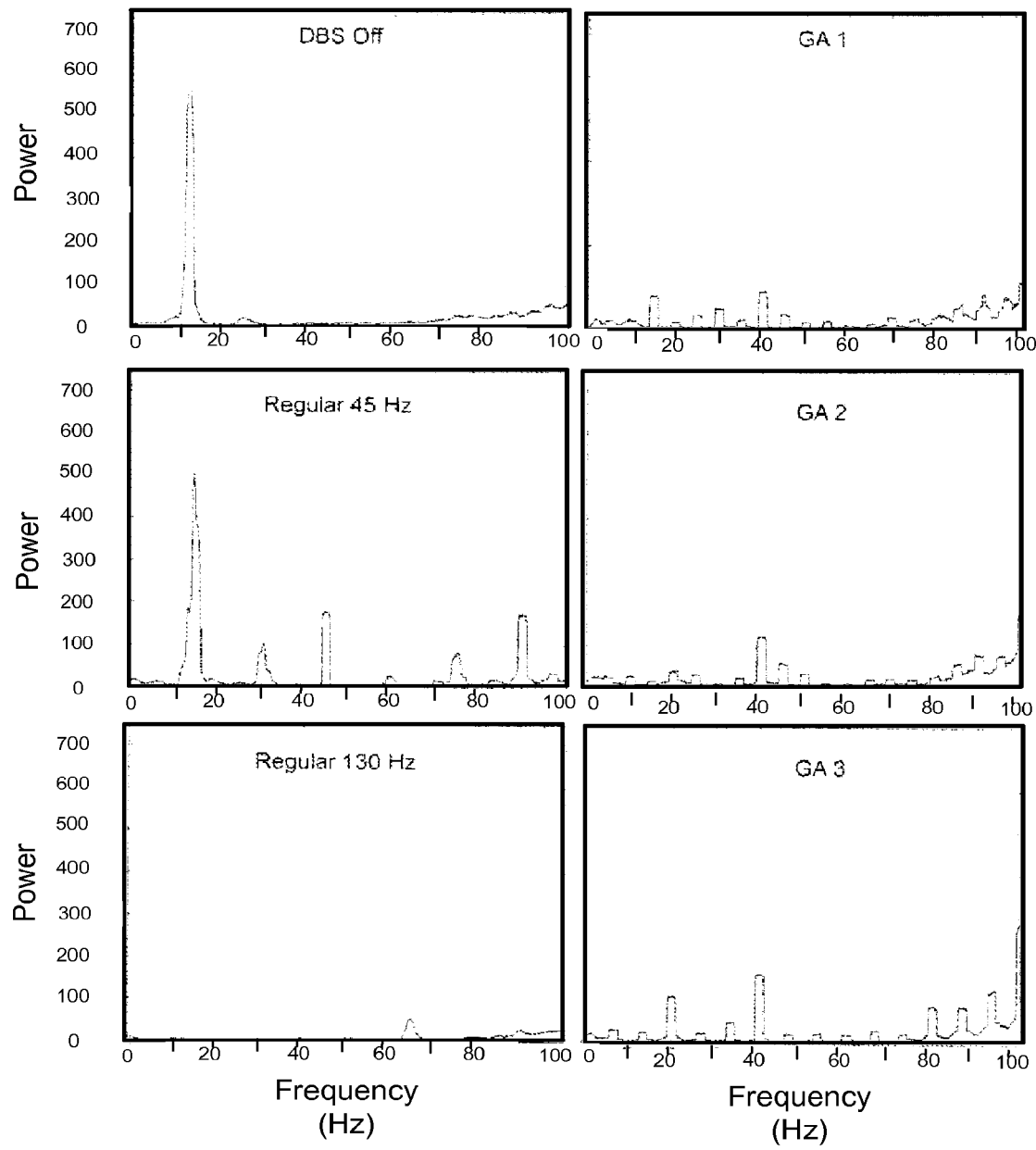
FIG. 26 includes graphs in the frequency domain of an average power of ten GPi neuronal firing sequences across a single iteration of the indicated stimulation, where such sequences were computer model generated.

FIG. 26 provides a spectral analysis of the average power across 10 GPi neurons for a single stimulation pattern iteration applying the indicated stimulation pattern to a forced Parkinsonian state in a model. As can be seen, there is significant oscillatory or synchronous activity generated around 15 Hz in the Parkinsonian state when the DBS input is off. The 45 Hz regular interval stimulation does not lessen such activity much, but the 185 Hz regular interval stimulation does. Accordingly, there may be a correlation between an attenuation of such oscillatory or synchronous activity and the effectiveness of a given DBS stimulation pattern. Indeed, it has been observed that such attenuation is at least correlated to an improvement in movement, especially in animals that have a previously demonstrated or induced state of bradykinesia.

Figure 27:
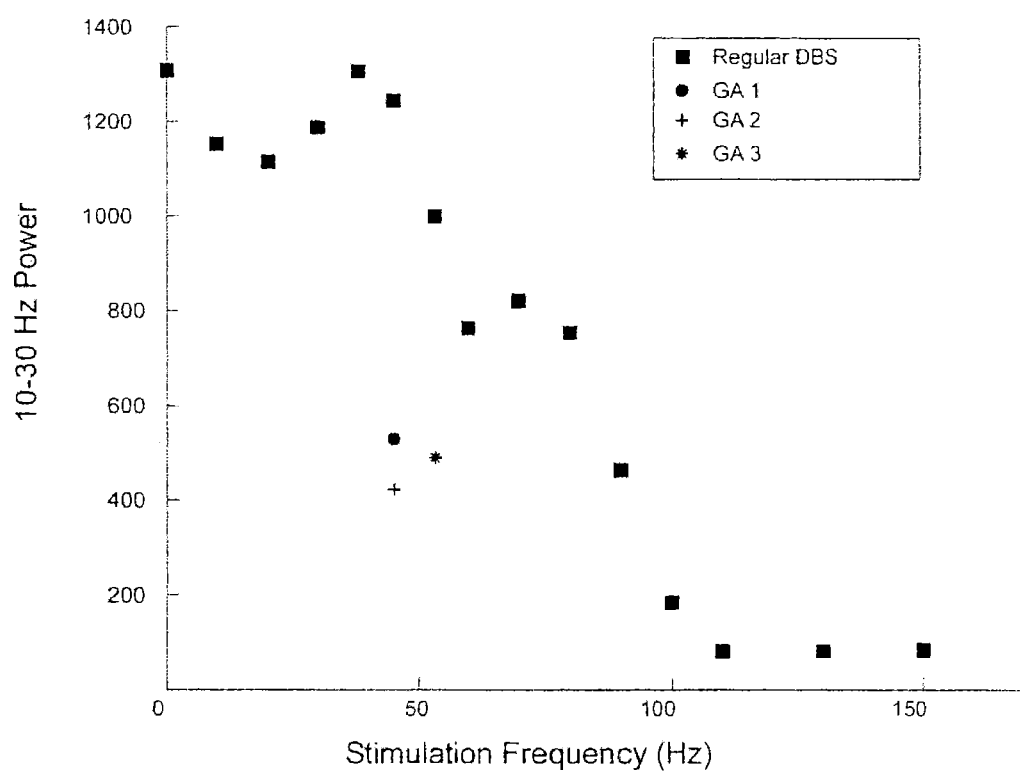
FIG. 27 is a tuning curve indicating the average power of ten GPi neuronal firing sequences across ten iterations of the indicated stimulation, where such sequences were computer model generated.

FIG. 27 provides an example tuning curve to analyze the 10-30 Hz global pallidus internal (GPi) neuronal power. That is, the spectra for 10 GPi neurons in a model were averaged for each stimulation state across 10 iterations. The plotted points indicate the average power of the GPi spike times across all 10 GPi neurons, averaged across the 10 stimulation iterations at each stimulation state. As can be seen, the power demonstrated in the 10-30 Hz frequencies by the GPi neurons (which are generally correlated to a neurological condition) is greatly reduced by the application of stimulation patterns that have been clinically shown to assist in reducing negative effects of such conditions. Accordingly, stimulation patterns according to the present invention may be, and have found to be, directed towards or involve the reduction of the average power of GPi oscillatory or synchronous activity. In fact, as shown in FIG. 27, an attenuation of at least about 25% of oscillatory activity caused by an actual animal neurological condition or a neurological condition model, but more preferably an attenuation of about 50% or greater, may be achieved using stimulation patterns according to the present invention.

The power of the oscillatory or synchronous activity that may be modeled, or measured from a patient, as correlated to a neurological condition may be used in alternative cost functions according to another embodiment of the present invention for optimizing stimulation patterns. One cost function that may be employed by an optimization algorithm or technique according to the present invention is as follows: $C=(P_{GA}-P_{FMReg})/P_{FMReg}*100\%$ where PGA is the average power generated by a computer model, over a given frequency range, of the firing of one or more GPi neurons when a selected generational stimulation pattern, which was initially created or generated by the genetic algorithm, is applied to the STN in the model and PFMReg is the power generated by a computer model, over the same given frequency range, of the firing the same GPi neurons when a DBS stimulation pattern of uniform frequency at a frequency equal to the average frequency of the GA train under analysis. The given frequency range may be a single frequency (e.g. 15 Hz) or a set of preferably contiguous frequencies (e.g. 10-30 Hz) or a set of noncontiguous frequencies (e.g. 15, 20, and 30 Hz).

Another cost function, using oscillatory power, that may be used to optimize stimulation patterns is as follows: $C=W*P+K*f$, where C is the cost, P is the average power generated by a computer model, over a given frequency range, of the firing of one or more GPi neurons when a selected generational stimulation pattern, which was initially created or generated by the genetic algorithm, is applied to the STN in the model, f is the average frequency of the generational pattern of stimulation, W is an appropriate weighting factor for the average power, and K is an appropriate weighting factor for the frequency. The given frequency range may be a single frequency (e.g. 15 Hz) or a set of preferably contiguous frequencies (e.g. 10-30 Hz) or a set of noncontiguous frequencies (e.g. 15, 20, and 30 Hz). The weighting factors W and K allow quantitative differentiation between efficacy (as a function of P) and efficiency (as a function of f) to generate patterns of non-constant inter-pulse interval deep brain stimulation trains that provide advantageous results with lower average frequencies, compared to conventional constant frequency pulse trains.

The non-regular temporal patterns of stimulation generated and disclosed above therefore make possible achieving at least the same or equivalent (and expectedly better) clinical efficacy at a lower average frequency compared to conventional constant-frequency temporal patterns. The lower average frequencies of the non-regular temporal stimulation patterns make possible increases in efficiency and expand the therapeutic window of amplitudes that can be applied to achieve the desired result before side effects are encountered.

DBS is a well-established therapy for treatment of movement disorders, but the lack of understanding of mechanisms of action has limited full development and optimization of this treatment. Previous studies have focused on DBS-induced increases or decreases in neuronal firing rates in the basal ganglia and thalamus. However, recent data suggest that changes in neuronal firing patterns may be at least as important as changes in firing rates.

The above described systems and methodologies make it possible to determine the effects of the temporal pattern of DBS on simulated and measured neuronal activity, as well as motor symptoms in both animals and humans. The methodologies make possible the qualitative and quantitative determination of the temporal features of low frequency stimulation trains that preserve efficacy.

The systems and methodologies described herein provide robust insight into the effects of the temporal patterns of DBS, and thereby illuminate the mechanisms of action. Exploiting this understanding, new temporal patterns of stimulation may be developed, using model-based optimization, and tested, with the objective and expectation to increase DBS efficacy and increase DBS efficiency by reducing DBS side effects.

The invention provides non-regular stimulation patterns or trains that can create a range of motor effects from exacerbation of symptoms to relief of symptoms. The non-regular stimulation patterns or trains described herein and their testing according to the methodology described herein will facilitate the selection of optimal surgical targets as well as treatments for new disorders. The non-regular stimulation patterns or trains described herein make possible improved outcomes of DBS by potentially reducing side effects and prolonging battery life. The extended battery life will result from a lower average frequency of stimulation (45 Hz vs. 100 or 185 Hz), thereby delivering less electrical current over time. Surgeries to replace depleted pulse generators will be needed less frequently and the costs that a DBS patient can expect with the DBS system will be diminished.

The foregoing is considered as illustrative only of the principles of the invention. Furthermore, since numerous modifications and changes may readily occur to those skilled in the art, it is not desired to limit the invention to the exact construction and operation shown and described. While the preferred embodiment has been described, the details may be changed without departing from the invention. For instance, although the disclosed embodiments of an algorithm used to generate stimulation patterns is an evolutionary algorithm, namely a genetic algorithm, the scope of the methods for this technology is not limited to genetic algorithms. Indeed, the scope of the present invention includes other contemplated model-based optimization techniques including, but not limited to, other evolutionary algorithms, swarm intelligence algorithms, and other optimization techniques or metaheuristic. The scope of the present invention is not limited to any particular model of a neurological disorder, such as PD. Present or future models of neurological disorders that are treated with DBS, or other electrical stimulation, are candidates for use with the methods described herein. Furthermore, while certain electrical stimulation patterns have been clinically applied in an effort to quantify their efficacy and efficiency, it will be appreciated that the scope of the present invention is not necessarily limited to any particular stimulation pattern as disclosed, but rather the scope of the present invention encompasses all patterns generated according hereto. The claims as follows are intended to include all modifications and alterations insofar as they come within the scope of the claims or the equivalent thereof.

The invention claimed is:

1. A method of treating Parkinson's disease in a human being comprising:
   generating non-regular patterns of electrical stimulation having a frequency range between 100 Hz and 200 Hz and applying the non-regular patterns of electrical stimulation to a human being having Parkinson's disease via an implanted lead in the human being's thalamus, subthalamus, or globus pallidus;
   modeling oscillatory or synchronous activity in the human being; and
   generating subsequent non-regular patterns of electrical stimulation based on the modeled activity and applying the subsequent non-regular patterns of electrical stimulation to the human being via the implanted lead, wherein the subsequent non-regular patterns of electrical stimulation comprise a plurality of pulses having non-regular, non-random, differing inter-pulse intervals between the pulses.

2. The method of claim 1 wherein the frequency range is 130 Hz.

3. The method of claim 1 further comprising quantitatively assessing how thalamus transmitted motor commands are generated in the human being based upon the applied non-regular patterns of electrical stimulation prior to generating subsequent non-regular patterns of electrical stimulation.

4. The method of claim 3 wherein the quantitatively assessing step includes an error function reflecting how faithfully the thalamus transmitted motor commands are generated by inputs from the cortex of the human being.

5. The method of claim 3 wherein the quantitatively assessing includes optimizing stimulation patterns utilizes a cost function.

6. The method of claim 1 wherein the modeling employs a genetic algorithm.

7. The method of claim 6 wherein the genetic algorithm is coupled to a computational model of stimulation of the subthalamic nucleus.

8. The method of claim 1 wherein the modeling reflects neuronal firings of neurons in each of the subthalamic nucleus, the global pallidus exterior, and the global pallidus interior.

9. A method of treating Parkinson's disease in a human being comprising:
   generating non-regular patterns of electrical stimulation having a frequency range between 100 Hz and 200 Hz and applying the non-regular patterns of electrical stimulation to a human being having Parkinson's disease via an implanted lead in the human being's thalamus, subthalamus, or globus pallidus;
   measuring the oscillatory or synchronous activity in the human being;
   quantitatively assessing how thalamus transmitted motor commands are generated based upon the applied non-regular patterns of electrical stimulation; and
   generating subsequent non-regular patterns of electrical stimulation based on the measured activity and applying the subsequent non-regular patterns of electrical stimulation to the human being via the implanted lead, wherein the subsequent non-regular patterns of electrical stimulation comprise a plurality of pulses having non-regular, non-random, differing inter-pulse intervals between the pulses.

10. The method of claim 9 further comprising quantitatively assessing how thalamus transmitted motor commands are generated in the human being based upon the applied non-regular patterns of electrical stimulation prior to generating the subsequent non-regular patterns of electrical stimulation.

11. The method of claim 9 wherein the quantitatively assessing step includes an error function reflecting how faithfully the thalamus transmitted motor commands are generated by inputs from the cortex of the human being.

12. The method of claim 11 wherein the quantitatively assessing includes optimizing stimulation patterns includes a cost function.

13. The method of claim 9 further comprising modeling the oscillatory or synchronous activity in the human being via a genetic algorithm and wherein the subsequent non-regular patterns of electrical stimulation are based upon both the measured activity and the modeled activity.

14. The method of claim 13 wherein the genetic algorithm is coupled to a computational model of stimulation of the subthalamic nucleus.

15. The method of claim 13 further comprising modeling reflects neuronal firings of neurons in each of the subthalamic nucleus, the global pallidus exterior, and the global pallidus interior.

16. A method of treating epilepsy or movement disorders including dystonia in a human being comprising:
   generating non-regular patterns of electrical stimulation having a frequency range between 100 Hz and 200 Hz and applying the non-regular patterns of electrical stimulation to a human being having epilepsy or movement disorder including dystonia via an implanted lead in the human being's thalamus, subthalamus, or globus pallidus;
   modeling and/or measuring the oscillatory or synchronous activity in the human being;
   quantitatively assessing how thalamus transmitted motor commands are generated based upon the applied non-regular patterns of electrical stimulation; and
   generating subsequent non-regular patterns of electrical stimulation based on the modeling and/or measured activity and applying the subsequent non-regular patterns of electrical stimulation to the human being via the implanted lead, wherein the subsequent non-regular patterns of electrical stimulation comprise a plurality of pulses having non-regular, non-random, differing inter-pulse intervals between the pulses.

17. The method of claim 16 wherein the frequency range is 130 Hz.

18. The method of claim 16 wherein modeling is performed and includes a genetic algorithm.

19. The method of claim 18 wherein the genetic algorithm is coupled to a computational model of stimulation of the subthalamic nucleus.

\* \* \* \* \*